US009814555B2

(12) United States Patent
Nagale et al.

(10) Patent No.: US 9,814,555 B2
(45) Date of Patent: Nov. 14, 2017

(54) MEDICAL DEVICE FOR PELVIC FLOOR REPAIR AND METHOD OF DELIVERING THE MEDICAL DEVICE

(71) Applicant: Boston Scientific Scimed, Inc., Maple Grove, MN (US)

(72) Inventors: Sandra Nagale, Lowell, MA (US); Mark W. Boden, Harrisville, RI (US); John Wesley Sheets, Jr., Edina, MN (US); James M. Goddard, Pepperell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 480 days.

(21) Appl. No.: 14/204,969

(22) Filed: Mar. 11, 2014

(65) Prior Publication Data

US 2014/0275753 A1 Sep. 18, 2014

Related U.S. Application Data

(60) Provisional application No. 61/777,211, filed on Mar. 12, 2013.

(51) Int. Cl.
*A61F 2/00* (2006.01)

(52) U.S. Cl.
CPC ................................. *A61F 2/0045* (2013.01)

(58) Field of Classification Search
CPC .... A61F 2/0004; A61F 2/0036; A61F 2/0045; A61F 2/0031; A61F 2002/0068; A61F 2002/0081; A61F 2002/0086; A61F 2002/009; A61F 2002/0091
See application file for complete search history.

(56) References Cited

U.S. PATENT DOCUMENTS

| 2,687,131 A | 8/1954 | Raiche |
| 3,123,077 A | 3/1964 | Alcamo |
| 4,083,369 A | 4/1978 | Sinnreich |
| 4,324,331 A | 4/1982 | Ignasiak |
| 4,792,336 A | 12/1988 | Hlavacek et al. |
| 4,919,667 A | 4/1990 | Richmond |
| 4,998,912 A | 3/1991 | Scarbrough et al. |

(Continued)

FOREIGN PATENT DOCUMENTS

| DE | 10056169 A1 | 6/2002 |
| EP | 0088714 A1 | 9/1983 |

(Continued)

OTHER PUBLICATIONS

"Capio® Suture Capturing Devices", Reach, Throw and Capture: One Step. One Device., Boston Scientific, 2005, 4 pages.

(Continued)

*Primary Examiner* — Catherine B Kuhlman
(74) *Attorney, Agent, or Firm* — Brake Hughes Bellermann LLP

(57) ABSTRACT

In an embodiment, the invention discloses a medical device configured to be delivered and placed within a patient's body. The medical device includes an implant and a cover member. The implant is configured to be disposed within the patient's body. The implant includes a support member, a first arm member and a second arm member, an elongated first sleeve, and an elongated second sleeve. The support member includes a crescent shaped opening.

20 Claims, 11 Drawing Sheets

(56) References Cited

U.S. PATENT DOCUMENTS

| | | |
|---|---|---|
| 5,013,292 A | 5/1991 | Lemay |
| 5,082,112 A | 1/1992 | Dunklee |
| 5,112,344 A | 5/1992 | Petros |
| 5,149,329 A | 9/1992 | Richardson |
| 5,217,466 A | 6/1993 | Hasson |
| 5,217,486 A | 6/1993 | Rice et al. |
| 5,217,494 A | 6/1993 | Coggins et al. |
| 5,263,969 A | 11/1993 | Phillips |
| 5,356,432 A | 10/1994 | Rutkow et al. |
| 5,362,294 A | 11/1994 | Seitzinger |
| 5,383,905 A | 1/1995 | Golds et al. |
| 5,405,359 A | 4/1995 | Pierce |
| 5,425,747 A | 6/1995 | Brotz |
| 5,451,235 A | 9/1995 | Lock et al. |
| 5,458,609 A | 10/1995 | Gordon et al. |
| 5,458,636 A | 10/1995 | Brancato |
| 5,485,917 A | 1/1996 | Early |
| 5,527,341 A | 6/1996 | Gogolewski et al. |
| 5,534,008 A | 7/1996 | Acksel |
| 5,540,704 A | 7/1996 | Gordon et al. |
| 5,562,689 A | 10/1996 | Green et al. |
| 5,569,283 A | 10/1996 | Green et al. |
| 5,578,044 A | 11/1996 | Gordon et al. |
| 5,584,859 A | 12/1996 | Brotz |
| 5,611,515 A | 3/1997 | Benderev et al. |
| 5,643,311 A | 7/1997 | Smith et al. |
| 5,662,664 A | 9/1997 | Gordon et al. |
| 5,683,402 A | 11/1997 | Cosgrove et al. |
| 5,700,272 A | 12/1997 | Gordon et al. |
| 5,702,397 A | 12/1997 | Goble et al. |
| 5,713,910 A | 2/1998 | Gordon et al. |
| 5,720,761 A | 2/1998 | Kaali |
| 5,741,277 A | 4/1998 | Gordon et al. |
| 5,741,279 A | 4/1998 | Gordon et al. |
| 5,741,299 A | 4/1998 | Rudt |
| 5,840,011 A | 11/1998 | Landgrebe et al. |
| 5,871,488 A | 2/1999 | Tovey et al. |
| 5,899,909 A | 5/1999 | Claren et al. |
| 5,922,826 A | 7/1999 | Kuze et al. |
| 5,931,855 A | 8/1999 | Buncke |
| 5,948,001 A | 9/1999 | Larsen |
| 5,976,127 A | 11/1999 | Lax |
| 5,988,549 A | 11/1999 | Hitomi et al. |
| 6,010,447 A | 1/2000 | Kardjian et al. |
| 6,012,580 A | 1/2000 | Peters et al. |
| 6,039,686 A | 3/2000 | Kovac |
| 6,042,534 A | 3/2000 | Gellman et al. |
| 6,042,536 A | 3/2000 | Tihon et al. |
| 6,042,592 A | 3/2000 | Schmitt |
| 6,044,847 A | 4/2000 | Carter et al. |
| 6,048,351 A | 4/2000 | Gordon et al. |
| 6,096,051 A | 8/2000 | Kortenbach et al. |
| 6,102,921 A | 8/2000 | Zhu et al. |
| 6,195,646 B1 | 2/2001 | Grosh et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,224,616 B1 | 5/2001 | Kugel |
| 6,267,772 B1 | 7/2001 | Mulhauser et al. |
| 6,273,852 B1 | 8/2001 | Lehe et al. |
| 6,306,079 B1 | 10/2001 | Trabucco |
| 6,322,492 B1 | 11/2001 | Kovac |
| 6,328,686 B1 | 12/2001 | Kovac |
| 6,346,111 B1 | 2/2002 | Gordon et al. |
| 6,375,662 B1 | 4/2002 | Schmitt |
| 6,382,214 B1 | 5/2002 | Raz et al. |
| 6,406,423 B1 | 6/2002 | Scetbon |
| 6,454,778 B2 | 9/2002 | Kortenbach |
| 6,478,727 B2 | 11/2002 | Scetbon |
| 6,491,703 B1 | 12/2002 | Ulmsten |
| 6,502,578 B2 | 1/2003 | Raz et al. |
| 6,506,190 B1 | 1/2003 | Walshe |
| 6,530,943 B1 | 3/2003 | Hoepffner et al. |
| 6,544,273 B1 | 4/2003 | Harari et al. |
| 6,547,800 B2 | 4/2003 | Foerster et al. |
| 6,551,329 B1 | 4/2003 | Kortenbach et al. |
| 6,565,580 B1 | 5/2003 | Beretta |
| 6,575,998 B2 | 6/2003 | Beyar |
| 6,582,443 B2 | 6/2003 | Cabak et al. |
| 6,592,515 B2 | 7/2003 | Thierfelder et al. |
| 6,592,610 B2 | 7/2003 | Beyar |
| 6,595,911 B2 | 7/2003 | Lovuolo |
| 6,596,001 B2 | 7/2003 | Stormby et al. |
| 6,599,235 B2 | 7/2003 | Kovac |
| 6,599,310 B2 | 7/2003 | Leung et al. |
| 6,612,977 B2 | 9/2003 | Staskin et al. |
| 6,638,209 B2 | 10/2003 | Landgrebe |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau et al. |
| 6,648,899 B2 | 11/2003 | Kalinski et al. |
| 6,648,921 B2 | 11/2003 | Anderson et al. |
| 6,652,450 B2 | 11/2003 | Neisz et al. |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,691,711 B2 | 2/2004 | Raz et al. |
| 6,695,855 B1 | 2/2004 | Gaston |
| 6,702,827 B1 | 3/2004 | Lund et al. |
| 6,730,110 B1 | 5/2004 | Harari et al. |
| 6,746,455 B2 | 6/2004 | Beyar et al. |
| 6,752,814 B2 | 6/2004 | Gellman et al. |
| 6,755,781 B2 | 6/2004 | Gellman |
| 6,808,487 B2 | 10/2004 | Migliari |
| 6,830,052 B2 | 12/2004 | Carter et al. |
| 6,848,152 B2 | 2/2005 | Genova et al. |
| 6,881,184 B2 | 4/2005 | Zappala |
| 6,890,338 B1 | 5/2005 | Davis et al. |
| 6,908,425 B2 | 6/2005 | Luscombe |
| 6,911,003 B2 | 6/2005 | Anderson et al. |
| 6,911,034 B2 | 6/2005 | Nobles et al. |
| 6,932,759 B2 | 8/2005 | Kammerer et al. |
| 6,936,052 B2 | 8/2005 | Gellman et al. |
| 6,936,054 B2 | 8/2005 | Chu |
| 6,936,952 B2 | 8/2005 | Takamine |
| 6,946,003 B1 | 9/2005 | Wolowacz et al. |
| 6,953,428 B2 | 10/2005 | Gellman et al. |
| 6,960,160 B2 | 11/2005 | Browning |
| 6,971,986 B2 | 12/2005 | Staskin et al. |
| 6,986,780 B2 | 1/2006 | Rudnick et al. |
| 6,991,597 B2 | 1/2006 | Gellman et al. |
| 7,011,688 B2 | 3/2006 | Gryska et al. |
| 7,025,772 B2 | 4/2006 | Gellman et al. |
| 7,048,682 B2 | 5/2006 | Neisz et al. |
| 7,056,333 B2 | 6/2006 | Walshe |
| 7,070,556 B2 | 7/2006 | Anderson et al. |
| 7,070,558 B2 | 7/2006 | Gellman et al. |
| 7,083,568 B2 | 8/2006 | Neisz et al. |
| 7,083,637 B1 | 8/2006 | Tannhauser |
| 7,090,686 B2 | 8/2006 | Nobles et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,122,039 B2 | 10/2006 | Chu |
| 7,131,943 B2 | 11/2006 | Kammerer |
| 7,131,944 B2 | 11/2006 | Jacquetin |
| 7,198,597 B2 | 4/2007 | Siegel et al. |
| 7,204,801 B2 | 4/2007 | Grocela |
| 7,204,802 B2 | 4/2007 | De Leval |
| 7,223,229 B2 | 5/2007 | Inman et al. |
| 7,226,407 B2 | 6/2007 | Kammerer et al. |
| 7,226,408 B2 | 6/2007 | Harai et al. |
| 7,229,453 B2 | 6/2007 | Anderson et al. |
| 7,235,043 B2 | 6/2007 | Gellman et al. |
| 7,244,260 B2 | 7/2007 | Koseki |
| 7,244,759 B2 | 7/2007 | Muller et al. |
| 7,267,645 B2 | 9/2007 | Anderson et al. |
| 7,291,104 B2 | 11/2007 | Neisz et al. |
| 7,351,197 B2 | 4/2008 | Montpetit et al. |
| 7,361,138 B2 | 4/2008 | Wagner et al. |
| 7,364,541 B2 | 4/2008 | Chu et al. |

(56) References Cited

U.S. PATENT DOCUMENTS

| | | |
|---|---|---|
| 7,402,133 B2 | 7/2008 | Chu et al. |
| 7,413,540 B2 | 8/2008 | Gellman et al. |
| 7,527,588 B2 | 5/2009 | Zaddem et al. |
| 7,878,970 B2 | 2/2011 | Goldberg |
| 2001/0049467 A1 | 12/2001 | Lehe et al. |
| 2002/0099259 A1* | 7/2002 | Anderson ............ A61F 2/0045 600/29 |
| 2002/0133236 A1 | 9/2002 | Rousseau |
| 2002/0151909 A1 | 10/2002 | Gellman et al. |
| 2002/0156489 A1 | 10/2002 | Gellman et al. |
| 2003/0023250 A1 | 1/2003 | Watschke et al. |
| 2003/0055313 A1 | 3/2003 | Anderson et al. |
| 2003/0078604 A1 | 4/2003 | Walshe et al. |
| 2003/0176762 A1* | 9/2003 | Kammerer ......... A61B 17/0469 600/30 |
| 2003/0191360 A1 | 10/2003 | Browning |
| 2003/0208208 A1 | 11/2003 | Chu |
| 2003/0220538 A1 | 11/2003 | Jacquetin |
| 2003/0225424 A1 | 12/2003 | Benderev |
| 2003/0233107 A1 | 12/2003 | Gellman et al. |
| 2003/0233108 A1 | 12/2003 | Gellman et al. |
| 2004/0015048 A1 | 1/2004 | Neisz et al. |
| 2004/0015177 A1 | 1/2004 | Chu |
| 2004/0034372 A1 | 2/2004 | Chu |
| 2004/0039246 A1* | 2/2004 | Gellman ............. A61F 2/0036 600/30 |
| 2004/0039453 A1 | 2/2004 | Anderson et al. |
| 2004/0059293 A1 | 3/2004 | Chu et al. |
| 2004/0068159 A1 | 4/2004 | Neisz et al. |
| 2004/0087970 A1 | 5/2004 | Chu et al. |
| 2004/0106847 A1 | 6/2004 | Benderev |
| 2004/0116944 A1 | 6/2004 | Chu et al. |
| 2004/0172048 A1* | 9/2004 | Browning ............ A61F 2/0063 606/151 |
| 2004/0181243 A1 | 9/2004 | Chu et al. |
| 2004/0186515 A1 | 9/2004 | Rosenblatt et al. |
| 2004/0225181 A1 | 11/2004 | Chu et al. |
| 2004/0231678 A1 | 11/2004 | Fierro et al. |
| 2004/0236356 A1 | 11/2004 | Rioux et al. |
| 2004/0249397 A1 | 12/2004 | Delorme et al. |
| 2004/0249473 A1 | 12/2004 | Delorme et al. |
| 2005/0027220 A1* | 2/2005 | Wagner ................ A61F 2/0045 602/4 |
| 2005/0038452 A1 | 2/2005 | Chu |
| 2005/0043580 A1* | 2/2005 | Watschke ............ A61F 2/0045 600/30 |
| 2005/0131391 A1 | 6/2005 | Chu et al. |
| 2005/0131392 A1 | 6/2005 | Chu et al. |
| 2005/0131393 A1 | 6/2005 | Chu et al. |
| 2005/0177022 A1 | 8/2005 | Chu et al. |
| 2005/0222589 A1 | 10/2005 | Chu |
| 2005/0222591 A1 | 10/2005 | Gingras et al. |
| 2005/0234291 A1 | 10/2005 | Gingras |
| 2005/0245787 A1 | 11/2005 | Cox et al. |
| 2005/0250977 A1 | 11/2005 | Montpetit et al. |
| 2005/0261545 A1 | 11/2005 | Gellman et al. |
| 2005/0261547 A1 | 11/2005 | Bouffier et al. |
| 2005/0278037 A1 | 12/2005 | Delorme et al. |
| 2006/0041263 A1 | 2/2006 | Chu et al. |
| 2006/0052801 A1 | 3/2006 | Dreyfuss et al. |
| 2006/0058575 A1 | 3/2006 | Zaddem et al. |
| 2006/0089525 A1 | 4/2006 | Mamo et al. |
| 2007/0173864 A1 | 7/2007 | Chu |
| 2009/0171143 A1* | 7/2009 | Chu ................... A61B 17/0401 600/37 |
| 2010/0256442 A1* | 10/2010 | Ogdahl ................ A61F 2/0045 600/30 |
| 2013/0030243 A1* | 1/2013 | Boden ................ A61L 31/048 600/37 |

FOREIGN PATENT DOCUMENTS

| | | |
|---|---|---|
| EP | 0141589 A1 | 5/1985 |
| EP | 0299158 A1 | 1/1989 |
| EP | 0362146 A1 | 4/1990 |
| EP | 0412664 A1 | 2/1991 |
| EP | 0567130 A1 | 10/1993 |
| EP | 0774240 A1 | 5/1997 |
| EP | 1201189 A2 | 5/2002 |
| EP | 1508305 A2 | 2/2005 |
| EP | 1520554 A2 | 4/2005 |
| EP | 1609439 A1 | 12/2005 |
| FR | 2785521 A1 | 5/2000 |
| FR | 2852817 A1 | 10/2004 |
| FR | 2852818 A1 | 10/2004 |
| FR | 2871365 A1 | 12/2005 |
| GB | 670349 | 4/1952 |
| JP | 06114067 A2 | 4/1994 |
| MX | PA04008407 A | 12/2005 |
| WO | 9609796 A2 | 4/1996 |
| WO | 9639948 A1 | 12/1996 |
| WO | 98/35632 A1 | 8/1998 |
| WO | WO9835616 A1 | 8/1998 |
| WO | 9843545 A1 | 10/1998 |
| WO | 9937216 A1 | 7/1999 |
| WO | 0009039 A1 | 2/2000 |
| WO | 00/74613 A1 | 12/2000 |
| WO | 0106951 A1 | 2/2001 |
| WO | 0152135 A1 | 7/2001 |
| WO | 0231681 A1 | 4/2002 |
| WO | 0232284 A2 | 4/2002 |
| WO | 0238079 A2 | 5/2002 |
| WO | 02/062237 A1 | 8/2002 |
| WO | 02058563 A1 | 8/2002 |
| WO | 02/078571 A2 | 10/2002 |
| WO | 03068107 A1 | 8/2003 |
| WO | 03073960 A1 | 9/2003 |
| WO | 03/092546 A2 | 11/2003 |
| WO | 03096928 A1 | 11/2003 |
| WO | 03096929 A1 | 11/2003 |
| WO | 2004012626 A1 | 2/2004 |
| WO | 2004016196 A2 | 2/2004 |
| WO | 2004091442 A2 | 10/2004 |
| WO | 2004091443 A2 | 10/2004 |
| WO | 2005051204 A1 | 6/2005 |
| WO | 2005/122721 A2 | 12/2005 |
| WO | 2005122954 A1 | 12/2005 |
| WO | 2006/046950 A1 | 5/2006 |
| WO | 2007/019374 A2 | 2/2007 |
| WO | 2007014240 A1 | 2/2007 |
| WO | 2007016698 A2 | 2/2007 |
| WO | 2007087132 A1 | 8/2007 |

OTHER PUBLICATIONS

"Transvaginal Suture Fixation to Cooper's Ligament for Sling Procedures", Capio (TM) CL, "Transvaginal Suture Fixation to Cooper's Ligament for Sling Procedures," Boston Scientific Microvasive product brochure, 2000, 4 pages.

Leron, et al., "Sacrohysteropexy with synthetic mesh for the management of uterovaginal prolapse", British Journal of Obstetrics and Gynaecology,108.3, 2001, 629-633.

Mahdavi, et al., "A biodegradable and biocompatible gecko-inspired tissue adhesive", PNAS, vol. 105, No. 7, Feb. 19, 2008, pp. 2307-2312.

* cited by examiner

MEDICAL DEVICE FOR PELVIC FLOOR REPAIR AND METHOD OF DELIVERING THE MEDICAL DEVICE

CROSS REFERENCE TO RELATED APPLICATION

This application is a Nonprovisional of, and claims priority to, U.S. Patent Application No. 61/777,211, filed on Mar. 12, 2013, entitled "A MEDICAL DEVICE FOR PELVIC FLOOR REPAIR AND METHOD OF DELIVERING THE MEDICAL DEVICE", which is incorporated by reference herein in its entirety.

FIELD

The present invention generally relates to bodily implants and more particularly to bodily implants and their methods of delivery and placement within a body of a patient for the treatment of pelvic floor disorder.

DESCRIPTION OF THE RELATED ART

Implant materials used to repair pelvic floor dysfunctions can be either biologic or synthetic to provide support to such as prolapsed organs. In some cases, both types of materials may have their disadvantages, for example, some biologic materials can be better integrated with tissues than synthetic materials, but may not provide the required strength to support the prolapsed organs. Additionally, some synthetic materials may result in long term complications such as mesh erosion, dyspareunia, and infection as opposed to biologic materials.

Therefore, some of the known implants are composed of several materials including synthetic materials as well as biologic materials rather than one material (either biologic or synthetic), wherein the synthetic material provides support and the biologic or biosynthetic material acts as an overlay material to ensure favorable tissue integration. Such implants may be ideally sterilized and packaged as combination devices such that a surgeon or an operator can take the implant out of the packaging right before implantation. As a consequence, in some cases, a concern in preparation of the combination devices arises, wherein the choice of the overlay biologic material dictates sterilization conditions. Thus, the overlay biologic material is limited to materials that can withstand sterilization and packaging conditions. As infection may be a concern, especially for transvaginal pelvic floor reconstruction implants, having limitations in packaging and sterilization conditions may not be desirable. In addition, in some cases, the implant may adhere to foreign materials during delivery trans-vaginally.

Therefore, in light of the above, there is a need for an implant and a suitable way to protect the implant during insertion and delivery to keep it clean and protected from any adhesion of foreign material.

SUMMARY

In an embodiment, the invention discloses a medical device configured to be delivered and placed within a patient's body. The medical device includes an implant and a cover member. The implant is configured to be disposed within the patient's body. The implant includes a support member, a first arm member and a second arm member, an elongated first sleeve, and an elongated second sleeve. The support member includes a crescent shaped opening. The first arm member and the second arm member are coupled to the support member such that the support member extends between the two arm members. The elongated first sleeve is configured to enclose the first arm member and the elongated second sleeve is configured to enclose the second arm member. The cover member includes a cavity for enclosing a portion of the support member and a crescent shaped opening which is sized to be larger than the crescent shaped opening of the support member.

In an embodiment, the invention discloses a medical device configured to be delivered and placed within a patient's body. The medical device includes an implant and a cover member. The implant includes a support member, a first arm member and a second arm member, and an elongated sleeve. The support member is configured to be disposed within the patient's body and provide support to a bodily portion. The first arm member and the second arm member are coupled to the support member such that the support member extends between the two arm members. The elongated sleeve is configured to enclose the first arm member. The cover member is configured to enclose a portion of the support member. The cover member includes seams defined for tearing the cover member to facilitate removal of the cover member from the body into pieces.

In an embodiment, the invention discloses a method for placing a medical device in a patient's body. The method comprises creating a bodily access for delivery the medical device inside a patient's body. The medical device includes an implant with two arm members and a support member extending between the two arm members. The two arm members are enclosed in respective elongated sleeves and the support member is enclosed in a cover member. The method includes inserting the medical device inside the patient's body. The method further includes attaching the implant with a bodily tissue proximate the uterus. The method further includes removing the elongated sleeves. The method further includes removing the cover member from the patient's body, after attaching the implant, along a vaginal incision.

BRIEF DESCRIPTION OF THE FIGURES

The invention and the following detailed description of certain embodiments thereof may be understood by reference to the following figures.

DETAILED DESCRIPTION

Detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting, but rather to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition).

In general, the invention is directed to systems, methods, and devices for treating pelvic floor disorder. However, the invention may be equally employed for other soft tissue repair purposes such as hernia repair, repair of skeletal muscle, connective tissue repair, and the like. As described below in various illustrative embodiments, the invention provides systems, methods, and devices employing a medical device including an implant such that the implant is configured to be placed within a patient's body to support pelvic organs for the treatment of pelvic disorders such as pelvic prolapse and the like.

The term patient may be used hereafter for a person who benefits from the medical device or the methods disclosed in the present invention. For example, the patient may be a person whose body receives the medical device disclosed by the present invention in a surgical treatment. For example, in some embodiments, the patient may be a human female, human male, or any other mammal.

The terms proximal and distal described in relation to various devices, apparatuses, and components as discussed in the subsequent text of the present invention are referred to with a point of reference. The point of reference, as used in this description, is a perspective of an operator. The operator may be a surgeon, a physician, a nurse, a doctor, a technician, and the like, who may perform the procedure of delivery and placement of the bodily implants into the patient's body as described in the present invention. The term proximal refers to an area that is closest to the operator. The term distal refers to an area that is farthest from the operator.

Figure 1:
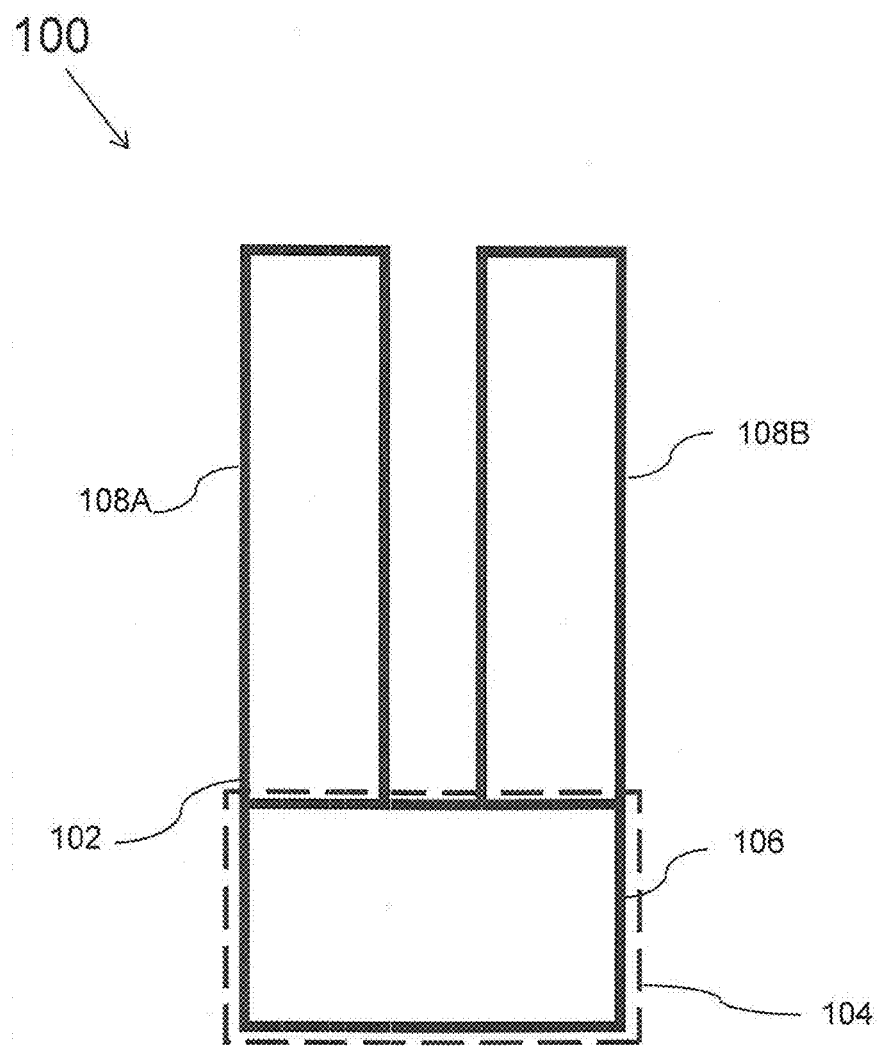
FIG. 1 is a schematic diagram of a medical assembly configured to be delivered into a patient's body for the treatment of pelvic floor disorder.

FIG. 1 is a schematic diagram of a medical device 100 configured to be delivered within a body of a patient, in accordance with an embodiment of the present invention. The medical device 100 includes an implant 102 and a cover member 104. The implant 102 includes a support member 106 and arm members 108A and 108B (hereafter collectively referred to as arm members 108). In an embodiment, the arm members 108 include a first arm member 108A and a second arm member 108B. The support member 106 is configured to be disposed within the body of the patient and provide support to a bodily portion. In some embodiments, the bodily portion is a pelvic organ of the patient such that the pelvic organ is supported by the support member 106. In other embodiments, the bodily portion can be any other disordered organ.

The support member 106 can be of different shapes, sizes, and configurations depending on the indented use of the medical device 100 and location of its placement within the body of the patient. In some embodiments, the support member 106 can be substantially rectangular, square, oval, or elliptical. The support member 106 can be shaped and sized in conformation to the pelvic organ of the patient where it is attached or stitched. In accordance with some embodiments, the support member 106 may be configured to conform to the shape of the body location where the support member 106 is intended to be attached. In some embodiments, the support member 106 includes a crescent shaped profile at a top portion which is configured to contact the uterus. The crescent shape, such as in the shape of a crescent moon helps the support member 106 to conform to the shape of the uterus of a patient's body during attachment. In embodiments, the profile at the top portion of the support member 106 can be of different shapes, and can define an opening of different sizes, and configurations for providing effective support to the uterus.

In embodiments, the arm members 108 can include the two arm members—the first arm member 108A and the second arm member 108B. The arm members 108 are coupled to the support member 106 such that the support member 106 extends between the arm members 108A and 108B. The arm members 108A and 108B are configured to be attached to bodily locations. The bodily locations can be a sacrum or tissues proximate to the sacrum or vaginal walls or sacrospinous ligament. In some embodiments, the bodily locations can be one of the bones or tissues at or proximate to the back of the pelvis. In some embodiments, the bodily locations can include a hip bone. In some embodiments, the bodily locations can include a coccyx. In some embodiments, the bodily locations can include a sacrospinous ligament or any other body location so as to provide adequate support to the disordered organ of the pelvic floor with the use of the support member 106. In some other embodiments, a third, fourth or even more arm members (not shown) similar to the arm members 108A and 108B can also be provided.

The arm members 108A and 108B can be of various shapes, sizes, and configurations, depending on the indented use of the medical device 100 and the location of its placement within the body of the patient. In some embodiments, the arm members 108A and 108B can be substantially planar, cylindrical, tubular, vasiform, cannular, and the like.

In some embodiments, the length of the second arm member 108B is lesser than the length of the first arm member 108A. In some embodiments, the length of the second arm 108B member is greater than the length of the first arm member 108A. In some embodiments, the length of the first arm member 108A and the length of the second arm member 108B can be same. In some embodiments, the second arm member 108B has width equal to the width of the first arm member 108A. In other embodiments, the widths of the second arm member 108B and the first arm member 108A are different.

In some embodiments, the arm members 108 are integral portions of the support member 106 such that the support member 106, and the arm members 108A and 108B form a single integral structure. In other embodiments, the arm members 108A and 108B are removably or fixedly coupled to the support member 106 by an operator. In some cases, the arm members 108A and 108B can be coupled to the support member 106 at two symmetric locations on either side of a central axis of the support member 106. In some cases, the arm members 108A and 108B can be coupled to the support member 106 at two diametrically opposite locations. In other embodiments, the arm members 108A and 108B can be attached to the support member 106 asymmetrically.

In some embodiments, elements such as sutures, adhesives, bonding agents, mechanical fasteners (e.g. a medical grade plastic clip), and the like may be used to couple the arm members 108A and 108B to the support member 106.

In an embodiment, the support member 106 and the arm members 108A and 108B are made up of synthetic polymeric materials such as polypropylene, polyvinylidene fluoride, polyethylene terephthalate or other polymers. These members may also include a bioresorbable component, which allows for the reduction in implanted mass, over time. The support member 106 and arm members 108A and 108B can also be constructed from allograft materials such as fetal bovine dermis, porcine dermis, or intestinal submucosa. The material of the arm members 108A and 108B and the support member 106 and especially of the support member 106 provides strength to the implant 102; thus, providing effective support to the pelvic organs for treatment. In an embodiment, the support member 106 and the arm members 108A and 108B are made up of a mesh. An example of the mesh utilized in the implant is similar to Uphold™ Mesh Assembly developed by the Boston Scientific Corporation. The Uphold™ Mesh Assembly utilizes a polypropylene mesh. The mesh is made from uncoated monofilament polypropylene fiber, which is knitted into a macro-porous structure. In some embodiments, the mesh can have a specified weight. For example, in some embodiments, the mesh weight can be approximately between 15 $g/cm^2$ to 35 $g/cm^2$ (e.g., 20 $g/cm^2$, 25 $g/cm^2$, 30 $g/cm^2$).

In some alternative embodiments, the support member 106 and the arm members 108A and 108B may also include a layer disposed over the support member 106 and the arm members 108A and 108B made up of a biological material or a biosynthetic material or a cadaveric tissue such as stem cells, natural xenograft material, collagen growth factors, and the like. This may facilitate favorable tissue integration.

In some embodiments, the implant is formed of a material that allows tissue in-growth after implantation. In some embodiments, the implant is made of a flexible material. In some embodiments, the implant is made of an elastic material. In some embodiments, the elastic and flexible synthetic material employed in the implant may allow stretching of the implant 102 without abdominal straining.

The implant 102 can be of various sizes (length, width, and thickness) depending on the intended use of a particular medical device 100 and the intended site of implantation. For example, the size of the support member 106 can depend on the size of the vaginal wall. Similarly, the size of the arm members 108 can have a length such that the support member 106 can be placed through and secured to the surrounding bodily tissues properly.

The cover member 104 is configured to enclose at least a portion of the support member 106. In some embodiments, the cover member 104 is configured to cover the entire support member 106. In some embodiments, the cover member 104 is configured to support a major or substantial part of the support member 106 as will be discussed later in conjunction with subsequent figures. In some embodiments, the cover member 104 is configured to enclose one or more arm members 108 in addition to the support member 106. For example, in some embodiments, the cover member 104 can enclose the first arm member 108A or the second arm member 108B or both. In some embodiments, even more arm members can be provided within the implant 102 such that the cover member 104 is configured to enclose even more arm members.

In embodiments, the cover member 104 may be removably or fixedly coupled to the support member 106 by an operator or surgeon at the time of surgery. In some embodiments, the cover member 104 may be temporarily attached to the support member 106 during delivery and placement of the implant 102 within the body and removed from the patient's body after surgery. In some embodiments, a solvent may be used to weaken and soften the cover member 104 such that the cover member 104 can be removed or pulled out after the implant 102 has been placed. Further, the solvent may have antimicrobial properties and may thus serve as an antimicrobial rinse. In some embodiments, the cover member 104 is permanently placed along with the implant 102 within the body of the patient. In such embodiments, the cover member 104, after implantation, may integrate with the tissue and erode over time. In such cases, the cover member 104 may facilitate initial healing of tissues.

In some embodiments, a physician may assemble the cover member 104 and the implant 102 by coupling such as by sling the implant 102 in the covering member. In some embodiments, the cover member 104 and the implant may alternatively be pre-assembled and the physician may use the pre-assembled implant 102. In an embodiment, the pre-assembled implant 102 and the cover member 104 can be packaged as a single kit. In another embodiment, the implant 102 and the cover member 104 are packaged separately.

In case of a removable cover member 104, in some embodiments, the cover member 104 may include seams defined for tearing the cover member 104 to facilitate removal of the cover member 104 into pieces from the body. In some embodiments, the seams are perforations or a series of openings or holes. In some embodiments, the seams may be provided longitudinally at several locations on the cover member 104 so as to cut the cover member 104 in several longitudinal pieces. In some embodiments, the seams may be provided horizontally along the circumference of the cover member 104 so as to tear the cover member 104 along the horizontal seams into several pieces. In some embodiments, one or several longitudinal and horizontal intersecting seams may be provided so as to tear the cover member 104 into several small pieces, facilitating removal of the small pieces from the body. In some embodiments, the cover member 104 may be scored or define a series of openings to facilitate the tearing of the cover member 104 into smaller pieces. In some embodiments, the cover member 104 may include a biodegradable portion or a portion that is configured to dissolve when contacted by bodily fluid to help facilitate the removal or tearing of the cover member 104.

In some embodiments, the cover member 104 is configured to keep the implant 102 sterile during and after delivery and implantation of the implant 102 within the patient's body. The cover member 104 keeps the implant 102 clean by avoiding any direct contact of a foreign material such as mucus, bacteria, particles, and the like on the implant 102. Thus, the foreign material adheres to the cover member 104 only during passage through the bodily tissues. In some embodiments, the cover member 104 may minimize the implant 102 folding during implantation.

The cover member 104 can be of different shapes, sizes, and configurations, depending on the indented use of the medical device 100 and the location of its placement within the body of the patient. In some embodiments, the cover member 104 can be substantially rectangular, square, oval, or elliptical. The cover member 104 can be shaped and sized in conformation to the support member 106 and the arm members 108A and 108B that it is configured to enclose. In accordance with some embodiments, for example, the cover member 104 may be configured to conform to the shape of the support member 106 of the implant 102. In some examples, the cover member 104 may be configured in a pouch shape or like an envelope having a cavity or such that the support member 106 can be retained within the cavity of the pouch shaped cover member 104. In some embodiments, the cover member 104 can include a portion that is substantially cylindrical, tubular, vasiform, cannular, or of any other shape to conform to the shape of the arm members 108A and 108B.

In some embodiments, the cover member 104 may include an opening or a cut out at the top of the cover member 104. The opening at the top of the cover member 104 can be of different shapes, sizes, including but not limited to a crescent shaped opening, rectangular opening, triangular opening, circular opening or of any other shape. The opening at the top of the cover member 104 may be greater than the opening at the top of the support member 106. This avoids, at times undesirable, suturing or attachment of the cover member 104 with the bodily tissues while suturing and attaching the support member 106 with the bodily tissues. The operator can thus find enough space around the opening of the support member 106 to pass threads or sutures in and out of the support member 106 without threading the suture through the cover member 104.

In an embodiment, the cover member 104 may be made up of synthetic materials such as plastic, polypropylene mesh, polymers, and other plastic materials (including, but not limited to, synthetic polymeric materials such as polypropylene, polyvinylidene fluoride, polyethylene terephthalate or other polymers). In some embodiments, the cover member 104 is made of a synthetic polymeric impermeable sheet. Some examples of polymeric materials utilized in the cover member 104 can be such as block polymers such as Styrene Ethylene Butadiene Styrene (SIBS), Poly(styrene-butadiene-styrene) (SBS), Polycaprolactone (PCl), Polylactic Acid (PLA) and the like, polyesters, polyurethanes, polylactide, polycaprolactones, hyaluronic acid-based material, biosynthesized cellulose and their copolymers, and the like. In some embodiments, the cover member 104 can be made from a biological material or a biosynthetic material or a cadaveric tissue such as stem cells, natural xenograft material, collagen growth factors, and the like.

In an embodiment, the cover member 104 can be made of a biocompatible material. In addition, to biocompatibility, the material of the cover member 104 can be selected so as to minimize mesh folding at implantation. In an embodiment, the cover member 104 can be made of a material that integrates with tissues and erodes over time after implantation, enabling appropriate healing. For example, in some embodiments, the cover member 104 can be made of hyaluronic acid. In such cases, the implant 102 can be packaged separately from the cover member 104, in some embodiments. After implantation, the hyaluronic acid-based cover member 104 integrates with tissues and erodes over time, and the implant 102 provides the required support. Also, by placing the cover member 104 around the implant 102, the implant 102 can be made lighter, with such as smaller diameter filaments, larger pores or both such that there is more support due to a rigid material during healing than after the implant 102 is absorbed. In this way, the support member 106 becomes more conformable and adapts more readily to natural motions in the pelvic floor. In accordance with some other embodiments, the cover member 104 can be made of materials other than hyaluronic acid that can provide required properties as discussed above, without limitations.

Additionally, the cover member 104 may be coated, impregnated, loaded or formed with one or more materials such as drugs, proteins, antibiotics, growth factors or other active compounds to be eluted to an adjacent tissue, in accordance with several other embodiments.

In some embodiments, chemical bioadhesives such as starch, epoxies, and the like may be used to couple the cover member 104 to the implant 102. In other embodiments, elements such as sutures, adhesives, bonding agents, mechanical fasteners (e.g. a medical grade plastic clip), and the like may be used to couple the cover member 104 to the implant 102. In some embodiments, the cover member 104 is made of a flexible material. In some embodiments, the cover member 104 is made of an elastic material. In some embodiments, the coupling element, such as the adhesive, may be configured to biodegrade or dissolve when contacted by bodily fluid to help facilitate the removal of the cover member 104.

In some embodiments, the cover member 104 fits tightly or snugly over the implant 102. For example, in some embodiments, the cover member 104 may define a cavity that is substantially the same size as the implant 102. In some embodiments, the cover member 104 fits loosely over the implant 102. For example, in some embodiments, the cover member 104 defines a cavity that is larger than the implant 102.

In some embodiments, the cover member 104 is porous. In some embodiments, the cover member 104 may include an antibiotic or antimicrobials. In some embodiments, the cover member 104 includes a polymer mesh. In some embodiments, the cover member 104 includes or is formed by a woven or non-woven mesh material.

Figure 2:
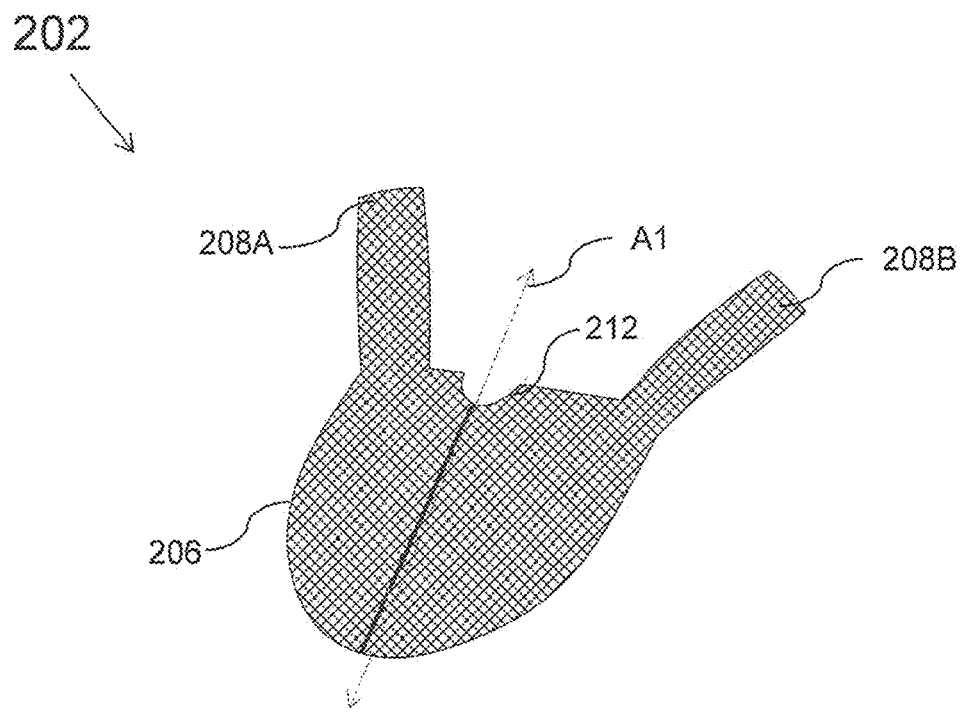
FIG. 2 is a perspective view of an implant configured to be placed within a patient's body, in accordance with an embodiment of the present invention.

FIG. 2 illustrates a perspective view of an implant 202 configured to be delivered into a patient's body for the treatment of pelvic floor disorder, in accordance with an embodiment of the present invention. The implant 202 includes a support member 206, and arm members 208A and 208B.

The support member 206 is configured to be disposed within a patient's body and provide support to the bodily portion. In some embodiments, the bodily portion is a pelvic organ of the patient, such as a uterus of the patient.

The support member 206 includes a crescent shaped profile 212 at a top portion which is configured to contact the uterus. The crescent shape, such as in the shape of a crescent moon helps the support member 206 to conform to the shape of the uterus (or a neck of the uterus) of a patient's body during attachment. The crescent shaped profile defines an opening 212. The opening 212 facilitates the support member 206 to conform to the shape of the uterus or bodily portion where it is placed. A shown, the opening has a crescent shape. In some other embodiments, the opening 212 can have any other shape.

The implant 102 includes two arm members referred to as a first arm member 208A and a second arm member 208B (hereafter collectively referred to as arm members 208A and 208B interchangeably). The arm members 208A and 208B are coupled to the support member 206 such that the support member 206 extends between the arm members 208A and 208B. The arm members 208A and 208B are configured to be attached around the bodily location as discussed with respect to the device of FIG. 1.

The arm members 208A and 208B can be of various different shapes, sizes, and configurations as discussed in FIG. 1. The first arm member 208A and the second arm member 208B can be shaped and sized to support the portion of the vaginal wall of the patient. In accordance with several embodiments, the first arm member 208A and the second arm member 208B may be configured to conform to the shape of the body of the patient. In accordance with the illustrated embodiment of FIG. 2, the arm members 208A and 208B may be configured as planar shaped strips of the implant material to help them conform to and wrap around the cervix or the uterus of the patient. In some other embodiments, the arm members 208A and 208B can be substantially cylindrical, tubular, vasiform, cannular, or of any other similar shape.

As shown, the first arm member 208A and the second arm member 208B can be coupled to the support member 206 at two symmetric locations on either side of a central axis A1 of the support member 206. In other cases, however, the first arm member 208A and the second arm member 208B can be coupled to the support member 206 at asymmetric locations.

In an embodiment, the support member 206 and the arm members 208A and 208B are made up of synthetic materials. Exemplary synthetic materials are discussed in conjunction with FIG. 1. The synthetic material of the arm members 208A and 208B, the support member 206, and especially of the support member 206 provides strength to the implant 202; thus, providing required support to the pelvic organs for treatment.

In some embodiments, the support member 106 and the arm members 108A and 108B include a mesh body that may be made up of a biological material or a biosynthetic material or a cadaveric tissue. Exemplary cadaveric tissue is discussed in conjunction with FIG. 1.

In some embodiments, the support member 206 and the first arm member 208A and the second arm member 208B are formed of a material that allows tissue in-growth after implantation. Various types of materials that can be employed to manufacture the implant have been described in conjunction with FIG. 1.

Figure 3:
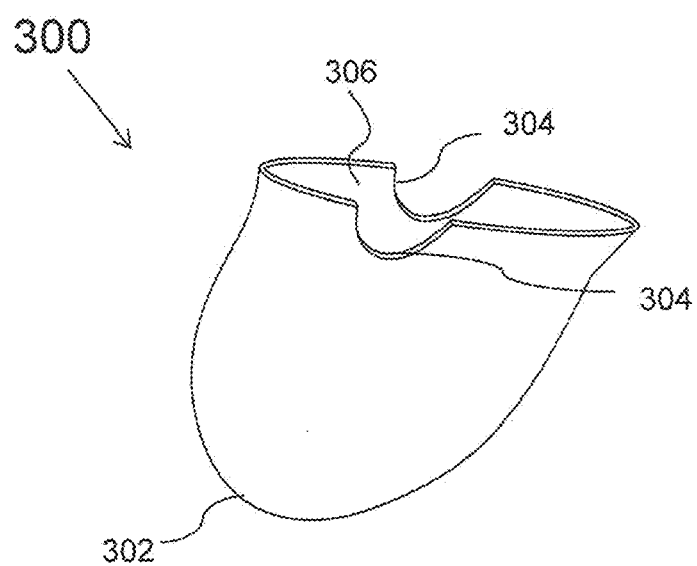
FIG. 3 is a perspective view of a covering member, in accordance with an embodiment of the present invention.

FIG. 3 illustrates a cover member 302 configured to enclose a portion of the support member 206 of FIG. 2, in an embodiment of the present invention. As shown in FIG. 3, the cover member 302 is configured to support a major or substantial part of the support member 206. FIG. 3 illustrates the cover member 302 configured to enclose the support member 206 only; however, in some embodiments, it can be configured to enclose the arm members also such as the arm members 208 of FIG. 2. In embodiments, the cover member 302 may be removably or fixedly coupled to the support member 206 by an operator or surgeon at the time of surgery. In some embodiments, the cover member 302 may be temporarily attached to the support member 206 during delivery and placement of the implant 202 within the body and removed from the patient's body after surgery.

The cover member 302 is configured to keep the implant 202 sterile during and after delivery and implantation of the implant 202 within the patient's body.

The cover member 302 as illustrated in FIG. 3 is configured in the shape of a pouch or envelope having a cavity 306 such that the support member 206 (as shown in FIG. 2) can be retained within the cavity 306 of the pouch shaped cover member 302. However, in some other embodiments, the cover member 302 can be of different shapes, sizes, and configurations, depending on the indented use of the medical device 200 and the location of its placement within the body of the patient and depending on the shape of the support member 206.

In some embodiments, the cover member 302 may include an opening 304 at the top of the cover member 302. The opening 304 at the top of the cover member 302 can be of different shapes, sizes, including but not limited to a crescent shaped opening, rectangular opening, triangular opening, circular opening or of any other shape. The opening at the top of the cover member 302 may be greater in size than the opening at the top of the support member 206. This avoids, at times undesirable, suturing or attachment of the cover member 302 with the bodily tissues while suturing and attaching the support member 206 with the bodily tissues. The operator can thus find enough space around the opening 212 of the support member 206 to pass threads or sutures in and out of the support member 206 without threading the suture through the cover member 302. In accordance with the illustrated embodiment two openings 304 are disclosed that are provided diametrically opposite. In some other cases, the cover member may include only one or more than two such openings. In an embodiment, the cover member 302 is made up of synthetic materials such as plastic, polypropylene, polymers, and other plastic materials. Exemplary polymeric materials are discussed in conjunction with FIG. 1.

Additionally, the cover member 302 may be coated, impregnated, loaded or formed with one or more materials such as drugs, proteins, antibiotics, growth factors or other active compounds to be eluted to an adjacent tissue, in accordance with several embodiments as discussed in FIG. 1. In an exemplary embodiment, the cover member 302 (of FIG. 3) is shown coupled to the implant 202 of FIG. 2A, in FIG. 4. In an embodiment, the cover member 302 of FIGS. 3 and 4 and the subsequent figures can be see-through or transparent. Various types of coupling arrangements may be used to couple the implant 202 with the cover member 302. Some of them are discussed later in subsequent figures.

Figure 5A:
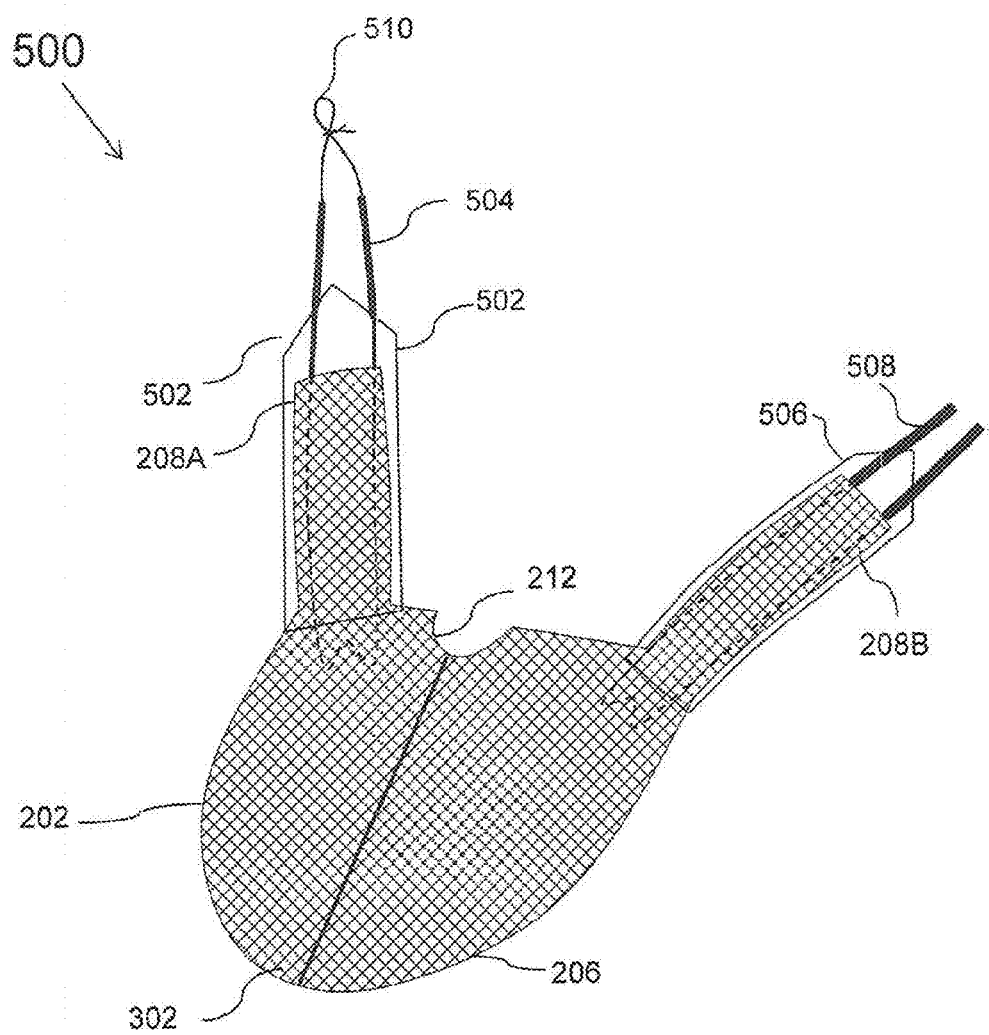
FIG. 5A illustrates a perspective view of the implant of FIG. 2 with an arm member coupled to a sleeve with the use of a suture, in accordance with an embodiment of the present invention.

FIG. 5A shows the implant 202 with the first arm member 208A being coupled to a first sleeve 502 such that the first sleeve 502 is an elongated sleeve and is configured to enclose the first arm member 208A and the second arm member 208B being coupled to a second sleeve 506 such that the second sleeve 506 is an elongated sleeve and configured to enclose the second arm member 208B. In embodiments, the elongated sleeves 502 and 506 have a shape different than the shape of the covering member 304. In some embodiments, the implant 202 can include even more arms such that all the arms can be coupled to sleeves. According to the illustrated embodiment of FIG. 5A, the first arm member 208A is coupled to the sleeve 502 with a single suture 504 and the second arm member 208B is coupled to the second sleeve 506 with the use of a suture 508. In some other embodiments, the arm members 208A and 208B can be coupled to the sleeves 502 and 506 by more than one suture or by using other modes of coupling. In some embodiments, the sutures 504 and 508 can define loops coupling the sleeves 502 and 508 to the arm member 208A and 208B respectively. For example, the suture 504, as shown in FIG. 5A, forms a loop 510. In an embodiment, one of the ends of the suture 504 in the form of the loop 510 and extending out of the sleeve 502 can be coupled to an insertion tool or a suturing device (such as a needle device) to place or suture the arm member 208A to a body location such as a sacrospinous ligament, and the like. Similarly, in some embodiments, one of the ends of the suture 508 can also be coupled to the suturing device.

In some embodiments, the arm member 208A and the support member 206 can be integral parts of a single component or implant. In some embodiments, the arm member 208A is removably attached to the support member 206. In such case, the arm members 208 can be coupled to the support member 206 with the use of such as a suture, in some embodiments. For example, the first arm member 208A can be coupled to the support member 206 with the use of a first suture and the second arm member 208B can be coupled to the support member with the use of a second suture. The first arm member 208A and the second arm member 208B can be configured to be decoupled from the support member 206 by cutting the first suture and the second suture, respectively. In some embodiments, a single suture may be used to couple the support member with the two arm members 208A and 208B. In some embodiments, the suture 504 that is used to couple the sleeve 502 with the first arm member 208A can extend further below to the support member 206 to couple the first arm member 208A to the support member 206.

Figure 5B:
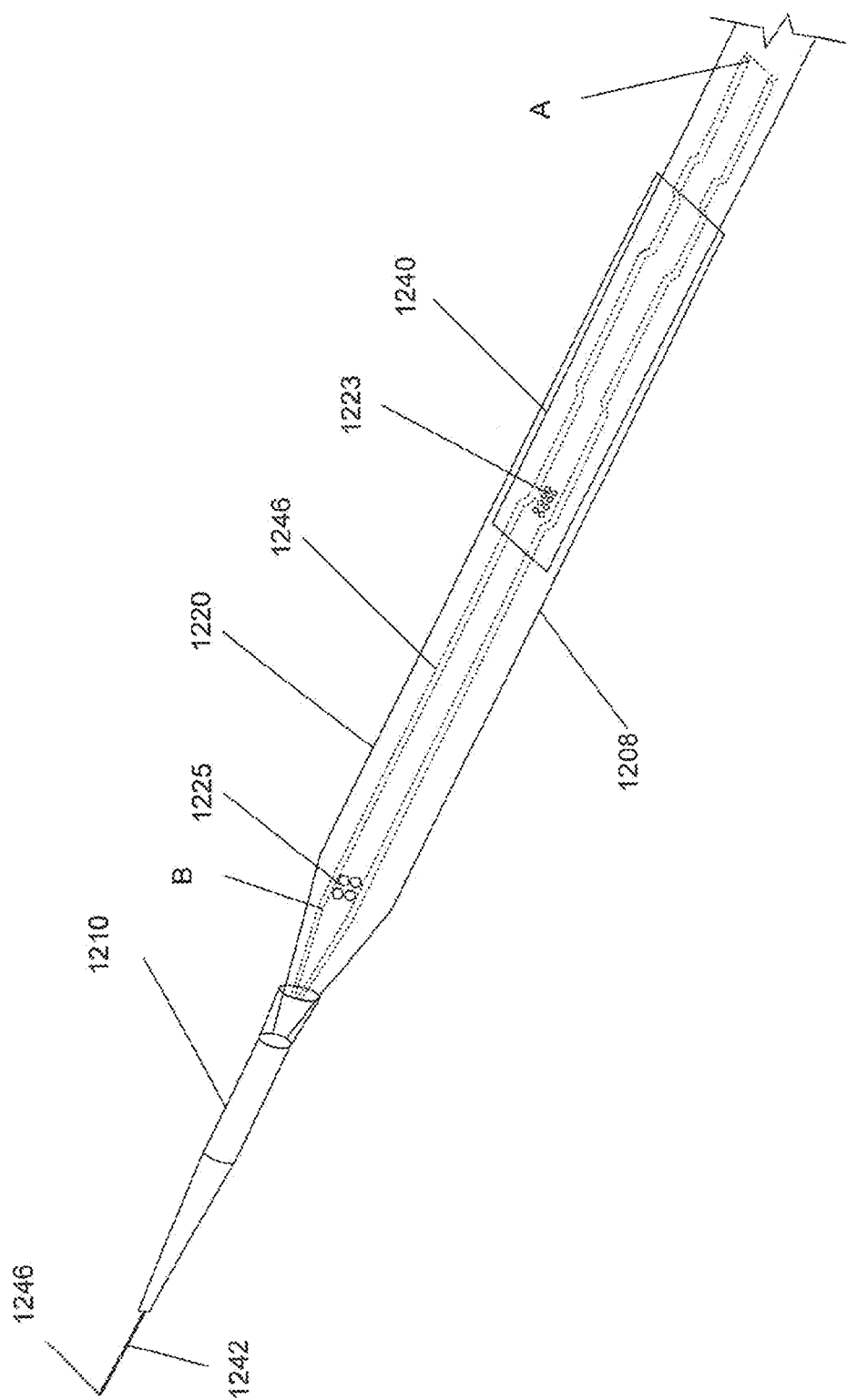
FIG. 5B illustrates an arm member in accordance with another embodiment of the present invention.

FIG. 5B illustrates an arm member 1208 according to another embodiment. The arm member 1208 can include a dilator 1210 and a sleeve 1220. In the illustrated embodiment, the dilator 1210 defines a lumen 1240. The dilator 1210 tapers from a first portion to a second portion. The dilator 1210 can be coupled to the sleeve 1220, for example, by crimping, heat sealing, stitching, stretching, tip tipping, etc. Alternatively, the sleeve 1220 can be formed to include a portion that forms a tapered dilator (e.g., the dilator and sleeve can be formed monolithically). The dilator 1210 can be used to expand or enlarge a passage during insertion through a tissue, to ease the transition to a cross-section or size of the sleeve 1220. The sleeve 1220 is also tapered, which also may help provide a lead-in through the bodily tissue.

The sleeve 1220 is secured to the first portion 1230 of the implant 1240 with a suture 1242. As shown in FIG. 5B, the suture 1242 is looped within the sleeve 1220 and weaved or threaded through the implant 1240 at location A. The suture 1242 can alternatively be coupled to the implant 1240 using any methods for coupling, for example, by crimping, heat sealing, stitching, etc. The strands of the suture 1242 form the loop through the sleeve 1220 extend into an interior of the dilator 1210 and can be crimped closed and heat bonded to an interior wall of the dilator 1220 to maintain the suture 1242 within the sleeve 1220.

The suture 1242 is coupled to and extends distally from the dilator 1210. Alternatively, a separate leader suture (separate from the suture 1242) can be used. A trocar needle 1246 is coupled to a distal end of the leader suture portion 1242 as shown in FIG. 5B. The trocar needle 1246 can be used to associate the dilator 1210 and implant 1240 to a delivery device. In other embodiments, the suture portion 1242 can form a loop at the distal end of the dilator 1210 to associate the dilator 1210 to a delivery device.

In the illustrated embodiment, a set of tacks or heat welds 1225 (four tacks or heat welds 1225 are shown, but other quantities can be used) are disposed between two strands of the looped suture 1242 and near a distal end of the sleeve 1220. The set of tacks 1225 couple a top wall and a bottom wall of the sleeve 1220 together, and maintain separation of the strands of the looped suture 1242 within the sleeve 1220. A second set of tacks or welds 1223 can be used to lightly secure the implant 1240 to the sleeve 1220. The separation of the strands of the suture 1242 enables or helps facilitate a cut to be made through a portion of the sleeve 1220 and only a single strand of the looped suture 1242 at, for example, location B, to remove the sleeve 1220 from the implant 1240 after being implanted within a pelvic region. Using a set or group of small tacks or welds (rather than a single large tack) can help maintain flexibility of the implant 1240 during delivery into a pelvic region where it may need to fold or bend during insertion.

Figure 6A:
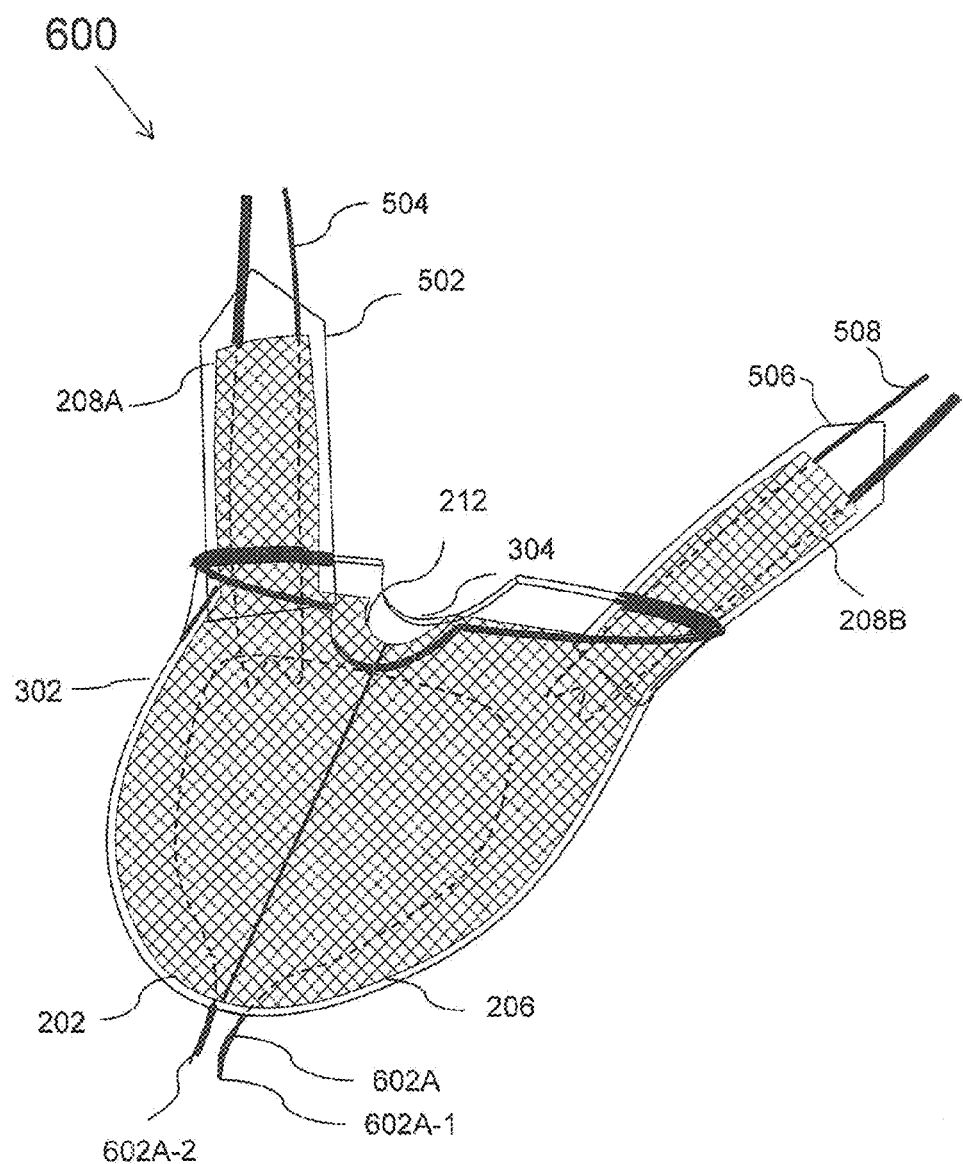
FIG. 6A illustrates a perspective view of the implant coupled to a cover member with the use of a suture, in accordance with an embodiment of the present invention.
Figure 6B:
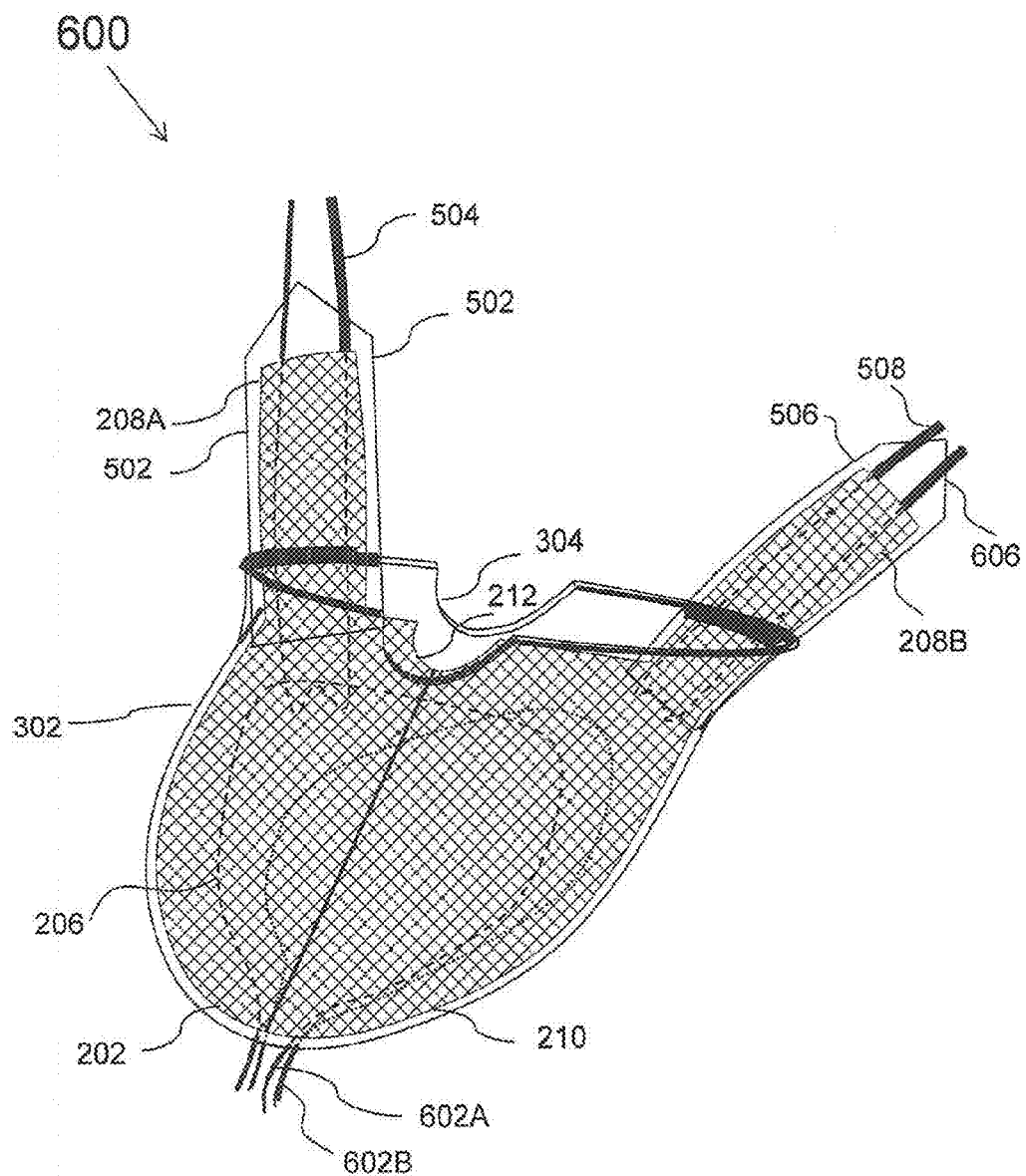
FIG. 6B illustrates a perspective view of the implant coupled to the cover member with two sutures, in accordance with an embodiment of the present invention.
Figure 6C:
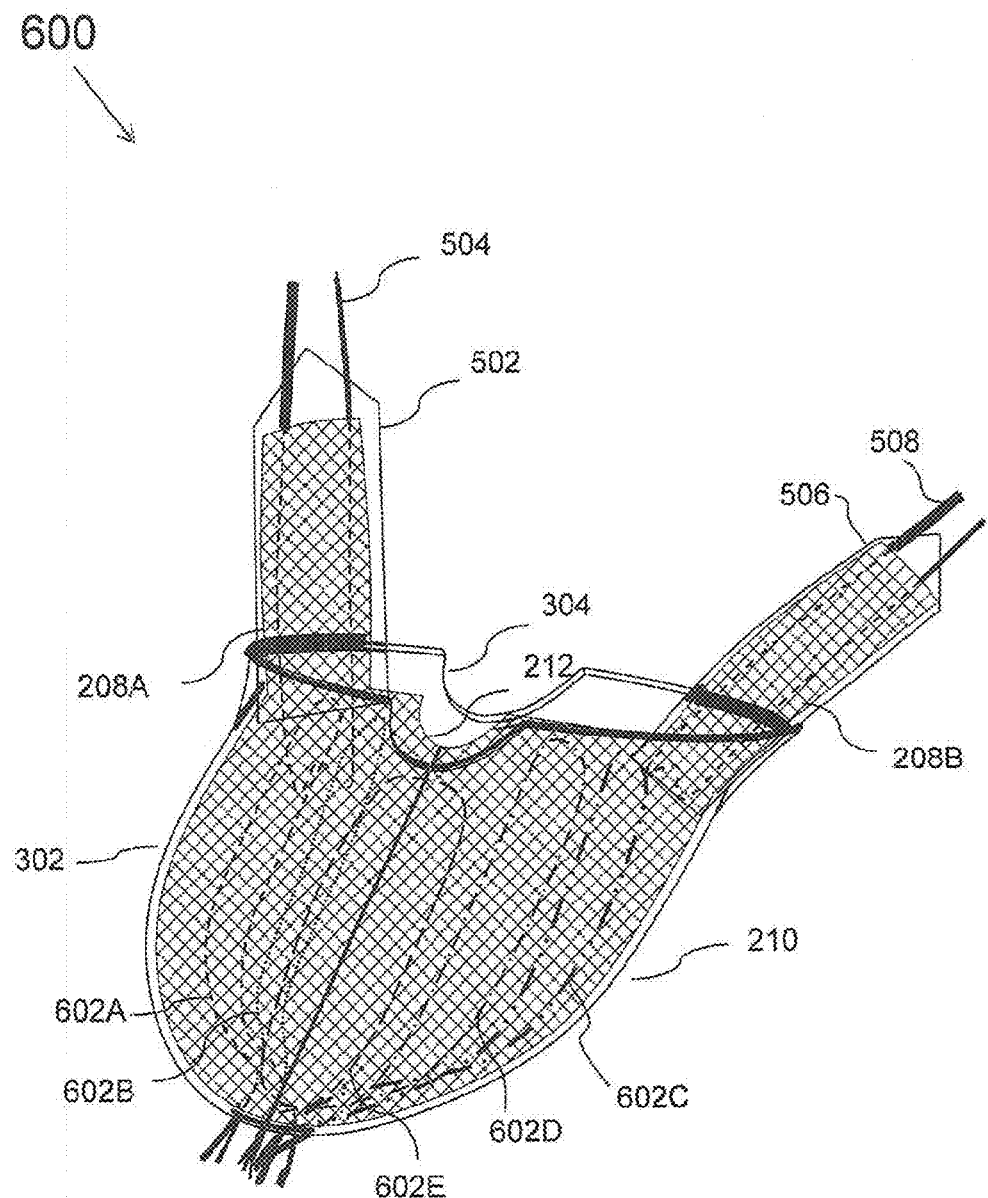
FIG. 6C illustrates a perspective view of the implant coupled to the cover member with the use of more than two sutures, in accordance with an embodiment of the present invention.

Referring to FIGS. 6A-6C, several exemplary ways of coupling the support member 206 with the cover member 302 with the use of a suture are disclosed. For example, as depicted in FIG. 6A, a single suture 602A is used to couple the support member 206 with the cover member 302. In an embodiment, the suture 602A can extend along the cover member 302 circumferentially and along four diametrically opposite longitudinal edges to couple it to the support member 206. The suture 602A may be a single suture with two free ends—602A-1 and 602A-2 such that one of the two free ends for example 602A-1 enters the cover member 302 and the support member 206 at an entry point (not shown) and surrounds the cover member 302 along at least some portion of the cover member 302 and the support member 206 longitudinally or horizontally before returning back to the entry point. For example, in an embodiment, as illustrated, the suture 602A extends to form a loop in a vertical direction. The suture 602A-1 comes out of the entry point and a knot can be formed thereby securing the free end 602A-1 to the free end 602A-2. The knot can be untied or cut by the operator and one of the free ends for example 602A-1 can be pulled in order to decouple the cover member 302 from the support member 206. In some embodiments, either of the two free ends 602A-1 and 602A-2 can be pulled in order to decouple the cover member 302 from the support member 206. The suture 602A can be interwoven into the support member 206 such as to keep the support member 206 flat. The weaving patterns and pressure points for the suture 602A can be selected such that during pulling of one of the free ends of the suture 602A, the support member 206 can be held in place.

In other embodiments, a tack weld or a heat weld (or a plurality of such welds) between the cover member and the support member may be used to temporarily couple the cover member to the support member. In some embodiments, a tack or heat weld is a coupling of a portion of the cover member with a portion of the support member by heating or otherwise melting a portion of at least one of the cover member and support member to weld or fuse the items together. The tack weld or heat weld may be configured to be released by pulling or forcing the cover member in a direction away from the support member. In such embodiments, the tack weld or heat weld would be configured to hold the cover member in place during delivery of the support member, but would allow the cover member to be removed without disrupting the position of the support member once the support member is correctly placed within the body of the patient. In yet other embodiments, an adhesive is used to couple a portion or portions of the cover member to the support member.

In accordance with another embodiment, as shown in FIG. 6B, two sutures 602A and 602B can be used to couple the support member 206 with the cover member 302. In some embodiments, the first suture 602A can extend circumferentially and vertically along a first portion of the support member 206 and the cover member 302 to form a loop, and the second suture 602B can extend along a second portion (may overlap the first portion) of the cover member 302 and the support member 206. The sutures 602A and 602B can each define two free ends such that one free end from each of the sutures 602A and 602B enters the cover member 302 and gets interwoven into the support member 206 so as to couple the cover member 302 to the support member 206. The first free end of each of the sutures 602A and 602B comes out of the entry point and forms a first bundle of suture ends.

While, decoupling the cover member 302 from the support member 206, any of the bundles of suture ends can be cut and pulled to remove the cover member 302 from the support member 206.

In accordance with still another embodiment, as shown in FIG. 6C, several sutures (more than two), for example, 5 sutures —602A, 602B, 602C, 602D, and 602E, can be used to couple the support member 206 with the cover member 302. The sutures 602A, 602B, 602C, 602D, and 602E each define two free ends such that one free end from each of the sutures 602A, 602B, 602C, 602D, and 602E enters the cover member 302 and gets interwoven into the support member 206 so as to couple the cover member 302 to the support member 206. The first free end of each of the sutures 602A, 602B, 602C, 602D, and 602E comes out of the entry point and forms a first bundle of suture ends. The sutures 602A, 602B, 602C, 602D, and 602E, in such embodiments, can extend along the support member 206 and the cover member 302 in and out along the longitudinal edges, or latitudinal edges and/or circumferentially around the support member 206 and the cover member 302 for coupling. In some embodiments, the cover member 302 is configured to be decoupled from the implant 202 upon cutting of the suture ends. In some embodiments, the sutures 602A, 602B, 602C, 602D, and 602E can be grouped together to form sets or bundles of sutures that can be used for coupling purposes.

In some embodiments, the sutures 602A-602E used for coupling the implant 202 with the cover member 302 may be interwoven with the implant 202 to keep them flat such that the sutures can be removed after the implant 202 has been placed within the bodily tissues. The weaving pattern and pressure points for the sutures 602A-602C are selected such that during pulling of one side of a suture or one of the sets or bundles of the sutures 602A-602C, the remaining sutures may hold the implant 202 flat against the bodily tissues. To ensure that the scaffold remains flat at the time when sutures are pulled out, the sutures are weaved through the scaffold horizontally or vertically such that each suture may be pulled in one of three directions at time of removal: left, right, or down. When the sutures are pulled (by pulling at them simultaneously as a bundle), there is always at least one of the sutures being pulled in one of the three directions at the same time; by doing so, the forces on the mesh are cancelled out and the mesh remains flat while sutures are being pulled. For example, 602C and 602E are woven horizontally in the mesh and 602D is woven vertically through the mesh. By pulling these sutures at the same time the pulling force on the mesh is experienced in all three directions (and in addition, the mesh is being held at the top by attachments to ligands), so the mesh is not pulled in any particular direction more than the other at any point in time while the envelope is being removed, this way the mesh stays flat during removal.

In an embodiment, the size of the crescent shaped opening 304 of the cover member 302 is larger than the size of the crescent shaped opening 212 of the support member 206. Therefore, the cover member 302 does not cover the opening 212 of the support member 206 and a portion of the support member 206 adjacent the opening 212. This provides sufficient area (adjacent the opening 212 on the support member 206) to place sutures for attaching the support member 206 with the body tissues without the sutures placed through the cover member 302.

In some embodiments, the arm member 208A, and/or the support member 206 is also coupled to the sleeve 502 by the suture 504 such that the suture 504 can be pulled out to decouple the sleeve 502 from the support member 206 and the arm member 208A. After implantation of the support member 206 inside patient's body, the cover member 302 and the sleeve 502 are removed. In some embodiments, the cover member 302 can be removed through a vaginal incision and the sleeve 502 can be removed through the vaginal incision or an abdominal incision.

Figure 4:
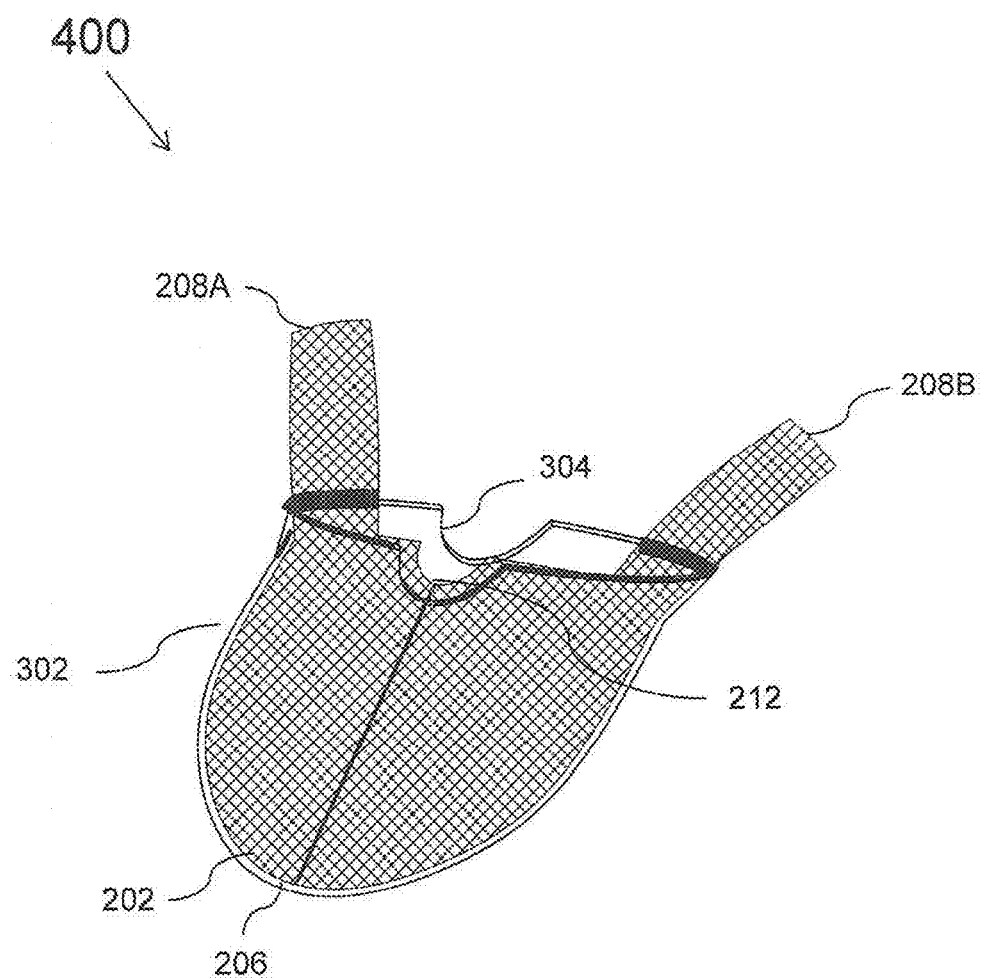
FIG. 4 is a perspective view of the covering member of FIG. 3 coupled to and enclosing the implant of FIG. 2, in accordance with an embodiment of the present invention.
Figure 7:
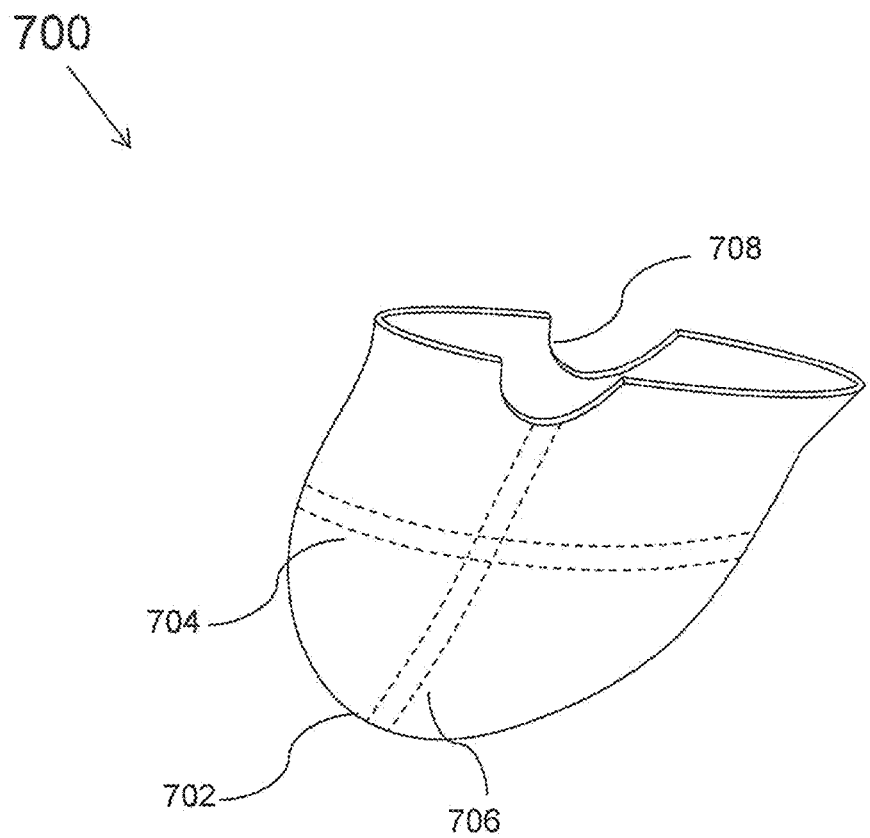
FIG. 7 is a perspective illustration of a covering member with seams, in accordance with an alternative embodiment of the present invention.

Referring to FIG. 7, in conjunction with FIGS. 2-4, an illustration of a cover member 702 is described.

In some embodiments, the cover member 702 may be temporarily attached to the support member 206 during delivery and placement of the implant 202 within the body and removed from the patient's body after surgery. In an embodiment, as shown in FIG. 7, the cover member 702 may include seams 704 and 706 defined for tearing the cover member 702 to facilitate removal of the cover member 702 from the body into pieces after implantation and fixation of the implant 202. In some embodiments, the seams 794, 706 can include such as perforations, openings, depressions, or indentations along a portion of the cover member. The cover member 702 may be cut along the seams 704 and 706. The seams 704 and 706 may be defined along the surface of the cover member 702 so as to facilitate the tearing of the cover member 702. In some embodiments, the cover member 702 may be cut at more than two locations along more than two seams such as to remove the cover member 702. The cover member 702 as illustrated in FIG. 7 is configured in the shape of a pouch having a cavity 708 such that the support member 206 can be retained within the cavity of the pouch-shaped cover member 702. Further, the cover member includes an opening or a notch or cut-out portion 708 that is configured to support the uterus or a neck of the uterus.

Figure 8:
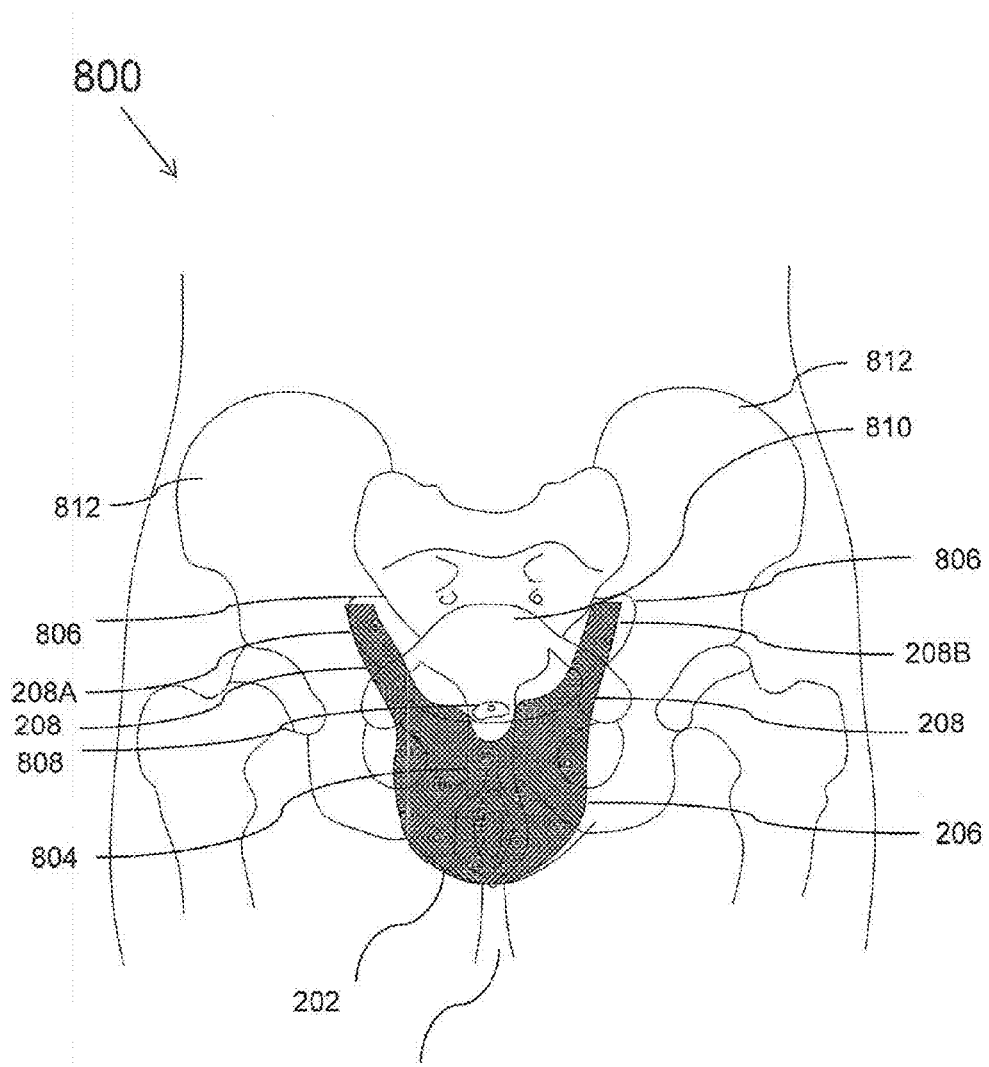
FIG. 8 illustrates placement of an implant within a patient's body, in accordance with an embodiment of the present invention.

FIG. 8 illustrates a schematic view of the implant 200 placed within a patient's body, in accordance with an embodiment of the present invention. FIG. 8 illustrates a view from a top side of a vaginal opening. The body portions of the patient such as a vagina (vaginal opening) 802, an anterior vaginal wall 804, a sacrospinous ligament 806, a cervix 808, a uterus 810 and hip 812 are illustrated in FIG. 8. The medical device 200 is hereafter used to describe the placement within the patient's body. However, other medical devices as described above may also be employed, in accordance with other embodiments of the present invention.

As illustrated in FIG. 8, the support member 206 is disposed or attached or stitched to a portion of the anterior vaginal wall 804 of the patient. In other embodiments, the support member 206 may be disposed or attached or stitched to a portion of the posterior vaginal wall (not shown in FIG. 8). In accordance with the illustrated embodiment, the support member 206 can be shaped and sized in conformation to the portion of the anterior vaginal wall 804 of the patient where it is disposed or attached or stitched. The support member 206 extends between the two arm members 208A and 208B. The first arm member 208A and the second arm member 208B are attached to the sacrum or close to the sacrum 806 or the sacrospinous ligament.

Figure 9:
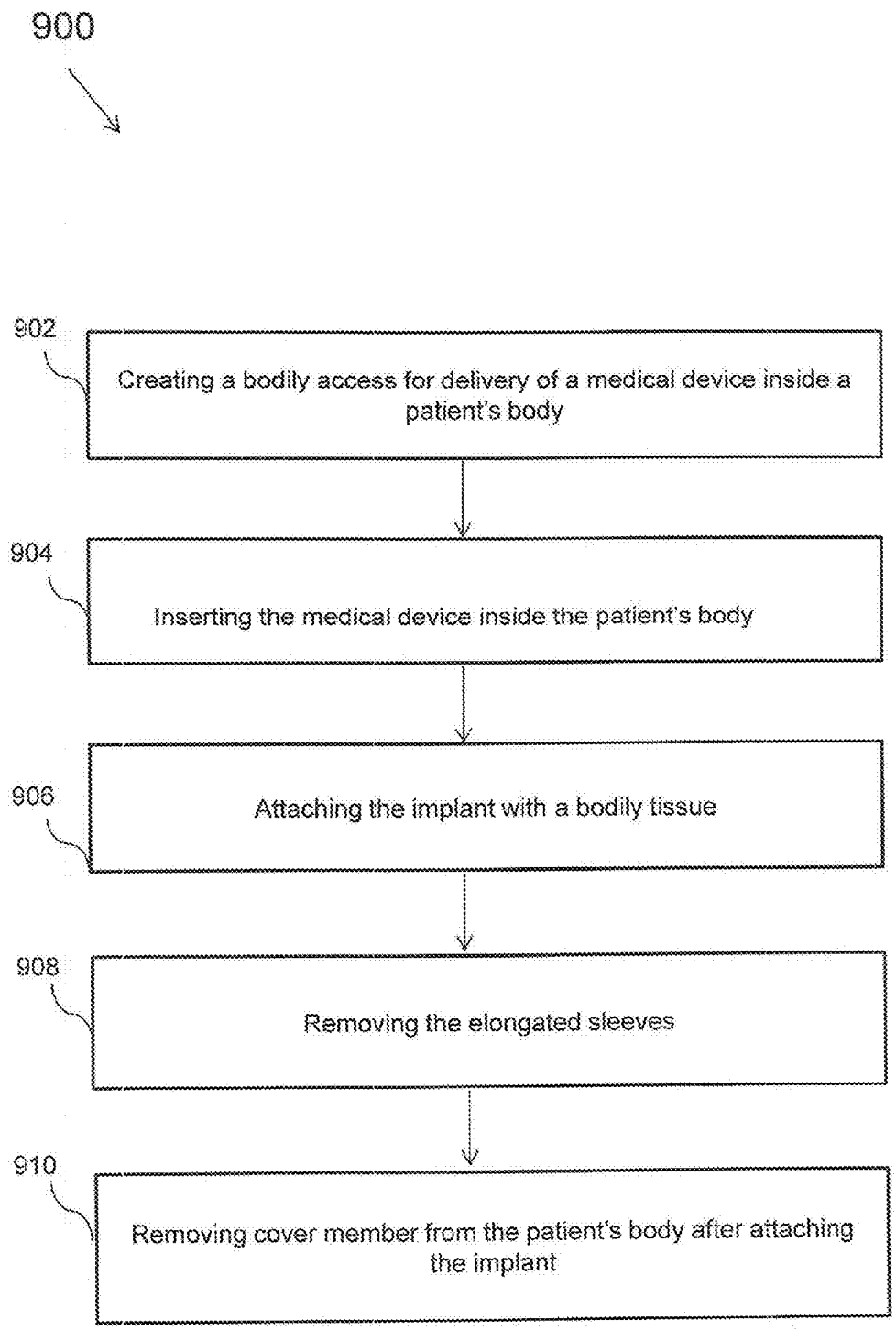
FIG. 9 is a flowchart illustrating a method of placing an implant within a patient's body, in accordance with an embodiment of the present invention.

FIG. 9 is a flowchart illustrating a method 900 of placement of the implant 202, in accordance with an embodiment of the present invention.

Referring now to FIG. 9 in conjunction with FIG. 8, the method 900 of placement of the implant 202 is described.

The method 900 includes creating a bodily access for delivery of the medical device inside a patient's body at step 902. In an embodiment, the access is created abdominally. In another embodiment, the access is created trans-vaginally. In accordance with various embodiments, an operator/surgeon may make incisions laproscopically, laprotomically, or in any other manner to create the required access to the vagina 802. In an embodiment, the implant 202 can be delivered and placed using an approach such as abdominal or laparoscopic sacrocolpopexy. Once the access to the vagina 802 is created, the medical device including the implant 202 and the covering member 302 is inserted into the patient's body at step 904.

In some embodiments, the method may further include attaching the implant 202 with a bodily tissue at step 906. The implant 202 can be attached with the bodily tissue such as through sutures or staples or using other means or elements. In embodiments, the implant 202 can be attached or stitched to the bodily tissues to provide support to a bodily portion. In some embodiments, the bodily portion is a pelvic organ of the patient such that the pelvic organ is supported by the support member 206. In other embodiments, the bodily portion is any other disordered organ of the patient such that the support member 206 is configured to support the disordered organ.

As discussed in conjunction with FIGS. 2-4, the support member 206 is disposed or attached or stitched to a vaginal wall 804 of the patient. In accordance with the illustrated embodiment, the support member 206 can be shaped and sized in conformation to the portion of the anterior vaginal wall 804 of the patient where it is disposed or attached or stitched. In some other embodiment, the support member 206 can be shaped and sized in conformation to the portion of the posterior vaginal wall of the patient where it is disposed or attached or stitched. The first arm member 208A and the second arm member 208B pass through and are attached to the sacrum or close to the sacrum 806 or sacrospinous ligament or muscles proximate the sacrospinous ligament. After attachment, an excess material of the arm members 208A and 208B can be cut off and removed.

In some embodiments, the implant may be coupled to the elongated sleeves such as 502 and 604 such as with the use of sutures as discussed above. In such cases, the method may include cutting the sutures for decoupling and removing the elongated sleeves 502 and 604 along such as an abdominal incision or a vaginal incision at step 908.

In some embodiments, the method further includes removing the cover member 302 from the patient's body after suturing of the implant 202 at step 910 such as through the vaginal incision. In some embodiments, the cover member 302 may be temporarily attached to the support member 206 during delivery and placement of the implant 202 within the body and removed from the patient's body after surgery. In some embodiments, the cover member 302 is sutured with the implant 202 using at least one suture. The method, in such cases, further comprises decoupling the cover member 302 from the implant 202 by cutting the suture. In some embodiments, a solvent may be used to weaken and soften the cover member 302 such that the cover member 302 can be removed or pulled out after the implant 202 has been sutured in place. As an exemplary scenario, the cover member 302 may include seams defined for tearing the cover member 302 to facilitate removal of the cover member 302 from the body as illustrated in FIG. 7. In other embodiments, removal of the cover member 302 may not be needed and the cover member 302 is placed permanently within the body. Additionally, the method may further include cutting and removing an undesired portion of the first arm member 208A and the second arm member 208B from the patient's body after placement. In some embodiments, the implant 202 may include a suture or multiple sutures coupling the arm members 208 with the support member 206 such that the arm members 208 are decoupled from the support member 206 by cutting the suture or sutures.

In some embodiments, a medical device configured to be delivered within a patient's body includes an implant and a cover member. The implant is configured to be disposed within the patient's body and includes a support member including a crescent shaped opening; a first arm member and a second arm member coupled to the support member such that the support member extends between the two arm members; an elongated first sleeve configured to enclose the first arm member; and an elongated second sleeve configured to enclose the second arm member. The cover member includes a cavity for enclosing a portion of the support member. The cover member includes a crescent shaped opening sized to be larger than the crescent shaped opening of the support member.

In some embodiments, the implant is configured for use in the treatment of pelvic floor disorders, the bodily portion being a pelvic organ supported by the support member. In some embodiments, the support member and the first arm member are made of a synthetic material. In some embodiments, the cover member is made of a synthetic polymeric impermeable sheet. In some embodiments, the cover member is made from one of a biologic and hyaluronic acid-based material. In some embodiments, the cover member is removable. The cover member includes seams defined for tearing the cover member to facilitate removal of the cover member from the body.

In some embodiments, the device includes a first suture couples the first arm member with the first elongated sleeve. The first arm member is configured to be decoupled from the first sleeve by cutting the first suture. In some embodiments, the device includes a second suture coupling the second arm member with the second elongated sleeve. The second arm member is configured to be decoupled from the second elongated sleeve by cutting the second suture.

In some embodiments, the device includes at least one suture coupling the implant to the cover member such that the cover member is configured to decouple the implant upon cutting of the at least one suture after placement and fixation of the implant at the bodily location. In some embodiments, the cover member includes a solvent configured to weaken and soften the cover member so as to facilitate removal of the cover member upon placement and suturing of the implant, the solvent further including antimicrobial properties.

In some embodiments, the crescent shaped opening of the support member is configured to be placed adjacent a uterus of the patient and shaped to conform to the shape of the uterus or a neck of the uterus.

In some embodiments, a medical device is configured to be delivered within a patient's body and includes and implant and a cover member. The implant includes a support member configured to be disposed within the patient's body and provide support to a bodily portion; a first arm member and a second arm member coupled to the support member such that the support member extends between the two arm members; and an elongated sleeve configured to enclose the first arm member. The cover member is configured to enclose a portion of the support member. The cover member includes seams defined for tearing the cover member to facilitate removal of the cover member from the body. In some embodiments, the cover member is made of a synthetic polymeric material. In some embodiments, the cover member is made from one of a biologic and hyaluronic acid-based material. In some embodiments, the support member and the first arm member is made of a synthetic material. In some embodiments, the elongated sleeve is a first sleeve, and the medical device further includes a second elongated sleeve configured to enclose the second arm member of the implant. The first elongated sleeve and the second elongated sleeve have a shape different than a shape of the cover member.

In some embodiments, a method for placing a medical device in a patient's body includes creating a bodily access for delivery the medical device inside a patient's body, the medical device including an implant with two arm members and a support member extending between the two arm members, wherein the two arm members are enclosed in respective elongated sleeves and the support member is enclosed in a cover member; inserting the medical device inside the patient's body; attaching the implant with a bodily tissue proximate the uterus; removing the elongated sleeves; and removing the cover member from the patient's body, after attaching the implant, along a vaginal incision.

In some embodiments, the support member and the two arm members are made of synthetic material. In some embodiments, the cover member is sutured with the implant using a suture, and the method includes decoupling the cover member from the implant by cutting the suture. In some embodiments, the elongated sleeves are coupled to the support member with the use of a suture, and the method includes cutting the suture for decoupling the elongated sleeves from the support member.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but it is to be understood in the broadest sense allowable by law.

What is claimed is:

1. A medical device configured to be delivered within a patient's body, the medical device comprising:
    an implant configured to be disposed within the patient's body and including:
        a support member including a first crescent shaped cutout;
        a first arm member and a second arm member coupled to the support member such that the support member extends between the first arm member and the second arm member;
        a first elongated sleeve configured to enclose the first arm member;
        a second elongated sleeve configured to enclose the second arm member; and
    a cover member including a closed end, an open end, and a cavity, the support member configured to be inserted into the cavity of the cover member via the open end, the cover member including a second crescent shaped cutout and a third crescent shaped cutout, the second crescent shaped cutout being sized to be larger than the first crescent shaped cutout of the support member, the third crescent shaped cutout being sized to be larger than the first crescent shaped cutout of the support member, the second crescent shaped cutout and the third crescent shaped cutout beingdisposed on opposite sides of the cover member along the open end.

2. The medical device of claim 1, wherein the implant is configured for use in the treatment of pelvic floor disorders, the implant configured to support a pelvic organ supported by the support member.

3. The medical device of claim 1, wherein the support member and the first arm member are made of a synthetic material, and the cover member is made of a synthetic polymeric impermeable sheet.

4. The medical device of claim 1, wherein first crescent shaped cut out is defined on an edge of the support member that extends between the first arm member and the second arm member.

5. The medical device of claim 1, wherein the cover member is made from one of a biologic and hyaluronic acid-based material.

6. The medical device of claim 1, wherein the cover member is removable, the cover member including seams defined for tearing the cover member to facilitate removal of the cover member from the patient's body.

7. The medical device of claim 1, further comprising a first suture that couples the first arm member with the first elongated sleeve, the first arm member being configured to be decoupled from the first elongated sleeve by cutting the first suture.

8. The medical device of claim 7, further comprising a second suture that couples the second arm member with the second elongated sleeve, the second arm member being configured to be decoupled from the second elongated sleeve by cutting the second suture.

9. The medical device of claim 1, further comprising at least one suture that couples the implant to the cover member such that the cover member is configured to be decoupled from the implant upon cutting of the at least one suture after placement and fixation of the implant within the patient's body.

10. The medical device of claim 1, wherein the cover member includes a solvent, the solvent configured to weaken and soften the cover member so as to facilitate removal of the cover member upon placement and suturing of the implant, the solvent including antimicrobial properties.

11. The medical device of claim 1, wherein the first crescent shaped cutout of the support member is configured to be placed adjacent a uterus of the patient and shaped to conform to the shape of the uterus or a neck of the uterus.

12. A medical device configured to be delivered within a patient's body, the medical device comprising:
    an implant including:
        a support member configured to be disposed within the patient's body and provide support to a bodily portion, the support member including a first cut out;
        a first arm member and a second arm member coupled to the support member such that the support member extends between the first arm member and the second arm member;

an elongated sleeve configured to enclose the first arm member; and a cover member having a closed end, an open end, and a cavity, the support member configured to be inserted into the cavity of the cover member via the open end, the cover member including seams on a surface of the cover member defined for tearing the cover member to facilitate removal of the cover member from the patient's body, the cover member including a second cut out and a third cut out disposed on opposite sides of the cover member along the open end, the second cut out and the third cut out being larger than the first cut out such that, when the support member is inserted into the cavity, the cover member does not cover a portion of the support member proximate to the first cut out.

13. The medical device of claim 12, wherein the cover member is made of a synthetic polymeric material.

14. The medical device of claim 12, wherein the cover member is made from one of a biologic and hyaluronic acid-based material, wherein the support member and the first arm member is made of a synthetic material.

15. The medical device of claim 12, wherein the seams include a first seam and a second seam, the second seam extending in a different direction on the surface of the cover member than the first seam.

16. The medical device of claim 12, wherein the elongated sleeve is a first elongated sleeve, the medical device further including a second elongated sleeve configured to enclose the second arm member of the implant, wherein the first elongated sleeve and the second elongated sleeve have a shape different than a shape of the cover member.

17. A method for placing a medical device in a patient's body, the method comprising:

creating a bodily access for delivery of the medical device inside a patient's body, the medical device including an implant with two arm members and a support member extending between the two arm members, the support member including a first cut out, wherein the two arm members are enclosed in respective elongated sleeves and the support member is enclosed in a cover member, the cover member having a closed end, an open end, and a cavity, at least a portion of the support member being inserted into the cavity of the cover member via the open end, the cover member including a second cut out and a third opening cut out disposed on opposite sides of the cover member along the open end, the second cut out and the third cut out being larger than the first cut out such that a portion of the support member proximate to the first cut out is not covered by the cover member;

inserting the medical device inside the patient's body;

attaching the implant with a bodily tissue proximate a uterus including attaching the portion of the support member that is not covered by the cover member to a vaginal wall;

removing the elongated sleeves; and removing the cover member from the patient's body via a vaginal incision.

18. The method of claim 17, wherein the support member and the two arm members are made of synthetic material.

19. The method of claim 17, wherein the cover member is sutured with the implant using a suture, the method further comprising decoupling the cover member from the implant by cutting the suture.

20. The method of claim 17, wherein the elongated sleeves are coupled to the support member with the use of a suture, the method further comprising cutting the suture for decoupling the elongated sleeves from the support member.

* * * * *